US012611124B2

(12) United States Patent
Whiting et al.

(10) Patent No.: US 12,611,124 B2
(45) Date of Patent: Apr. 28, 2026

(54) MONITORING APPARATUS AND METHOD

(71) Applicant: CURRENT HEALTH LIMITED,
Edinburgh (GB)

(72) Inventors: Stewart Whiting, Edinburgh (GB);
Samuel Moreland, Edinburgh (GB);
Hugh Carter, Edinburgh (GB);
Morgan Smith, Edinburgh (GB)

(73) Assignee: CURRENT HEALTH LIMITED,
Edinburgh (GB)

( * ) Notice: Subject to any disclaimer, the term of this
patent is extended or adjusted under 35
U.S.C. 154(b) by 0 days.

(21) Appl. No.: 18/415,732

(22) Filed: Jan. 18, 2024

(65) Prior Publication Data

US 2024/0148290 A1 May 9, 2024

Related U.S. Application Data

(62) Division of application No. 17/389,472, filed on Jul.
30, 2021, now Pat. No. 11,911,155.

(51) Int. Cl.
*A61B 5/1455* (2006.01)
*A61B 5/00* (2006.01)
*A61B 5/024* (2006.01)

(52) U.S. Cl.
CPC ...... *A61B 5/14552* (2013.01); *A61B 5/02438*
(2013.01); *A61B 5/14557* (2013.01); *A61B*
*5/6824* (2013.01); *A61B 5/6831* (2013.01)

(58) Field of Classification Search
CPC ............ A61B 5/14552; A61B 5/02438; A61B
5/14557; A61B 5/6824; A61B 5/6831;
A61B 5/02055; A61B 5/7207
See application file for complete search history.

(56) References Cited

U.S. PATENT DOCUMENTS

| | | | | |
|---|---|---|---|---|
| 9,642,529 B1 * | 5/2017 | Siddiqui | ............ | A61B 5/14552 |
| 2004/0034294 A1 * | 2/2004 | Kimball | ............... | A61B 5/0295 |
| | | | | 600/323 |
| 2004/0039254 A1 | 2/2004 | Stivoric | | |
| 2009/0259116 A1 * | 10/2009 | Wasserman | ........ | A61B 5/14551 |
| | | | | 600/323 |
| 2016/0058334 A1 * | 3/2016 | Takahashi | .............. | G16H 20/30 |
| | | | | 702/19 |

(Continued)

FOREIGN PATENT DOCUMENTS

| | | |
|---|---|---|
| EP | 3 488 781 | 5/2019 |
| EP | 3 556 289 | 10/2019 |
| JP | 2019-118460 | 7/2019 |

OTHER PUBLICATIONS

Edward D. Chan , Michael M. Chan, Mallory M. Chan, "Pulse
oximetry: Understanding its basic principles facilitates appreciation
of its limitations" Mar. 13, 2013, Respiratory Medicine (2013) 107,
789e799 (Year: 2013).*

*Primary Examiner* — Abid A Mustansir
(74) *Attorney, Agent, or Firm* — Nixon & Vanderhye P.C.

(57) ABSTRACT

An apparatus for monitoring blood oxygen saturation of a
subject is provided. The apparatus includes a unit configured
for wearing on the subject's upper arm, the unit comprising
first and second light sources configured to emit light of first
and second wavelengths and a photodetector configured to
detect light of the first and second wavelengths, where the
light sources are arranged to direct light into the upper arm
and the photodetector is arranged to detect light reflected
from within the upper arm.

8 Claims, 13 Drawing Sheets

(56)             References Cited

U.S. PATENT DOCUMENTS

2017/0055573  A1     3/2017  Utley
2017/0172435  A1*    6/2017  Presura .............. A61B 5/02416
2023/0030071  A1     2/2023  Whiting et al.

\* cited by examiner

MONITORING APPARATUS AND METHOD

CROSS REFERENCE TO RELATED APPLICATIONS

This application is a divisional application of U.S. application Ser. No. 17/389,472, filed Jul. 30, 2021, the entire disclosure of which is hereby incorporated herein by reference.

FIELD OF THE INVENTION

The present invention relates to the field of wearable apparatuses for monitoring physiological parameters of a subject and methods of monitoring physiological parameters using such apparatuses.

BACKGROUND TO THE INVENTION

It is desirable to automatically determine the blood oxygen saturation (or an indicator thereof) of a subject to facilitate monitoring over a period of time. Blood oxygen saturation is important because tissues throughout the body rely on the continuous delivery of oxygen to support metabolic function. Blood oxygen saturation is a vital sign and certain conditions (e.g. chronic obstructive pulmonary disease (COPD)) can lead to reduced blood oxygen saturation, as can high altitude, and carbon monoxide poisoning, for example. Where low blood oxygen saturation levels are persistent, this can lead to tissue damage.

Blood oxygen saturation reflects the percentage of oxygen bound to haemoglobin in arterial blood ($SaO_2$) and in peripheral arterial blood ($SpO_2$). In most cases, $SaO_2$ and $SpO_2$ should be very similar. $SaO_2$ can be measured by drawing blood from an artery and analysing the blood in a blood gas analyser machine. This is an accurate method; however it is time consuming and painful.

$SpO_2$ can be measured non-invasively using pulse oximetry. Typically this is carried out with a transmissive mode fingertip probe pulse oximeter which uses a light source to shine light through the fingertip and a photodetector to measure how much of the light reaches the opposite side of the fingertip, to determine how much of the light is absorbed in the oxygenated blood and tissue within the fingertip. Such fingertip probes are however inconvenient and cannot be worn continuously by a subject during day-to-day activities. Fingertip probes are therefore unsuitable for continuous monitoring of an ambulatory subject.

It is in this context that the present disclosure has been devised.

SUMMARY OF THE INVENTION

According to a first aspect of the invention, there is provided apparatus for monitoring blood oxygen saturation of a subject, the apparatus comprising a unit configured for wearing, the unit comprising:

a first light source configured to direct light of a first wavelength towards the upper arm when the unit is worn on the upper arm;

a second light source configured to direct light of a second wavelength towards the upper arm when the unit is worn on the upper arm, the second wavelength being different to the first wavelength; and one or more photodetectors, each configured to output a (e.g. at least one) detected light signal indicative separately of detection (e.g. by the or each of the one or more photodetectors) of light of the first wavelength and light of the second wavelength reflected from within the upper arm when the unit is worn on the upper arm, wherein the apparatus comprises one or more processors and a memory including instructions which, when executed by the one or more processors, causes the apparatus to:

determine an indicator of blood oxygen saturation of blood in the upper arm, in dependence on the (e.g. at least one) detected light signal, and optionally output the indicator of blood oxygen saturation. The unit may be a unit for wearing on the subject's upper arm.

Haemoglobin in the blood absorbs different wavelengths of light in different amounts. As such, an apparatus having first and second light sources configured to emit light of respective first and second wavelengths where the first wavelength is different to the second wavelength, and a photodetector configured to detect the first and second wavelengths is convenient, painless, and non-invasive way to determine an indicator of blood oxygen saturation.

It will be understood that the first wavelength is typically a peak or central wavelength, optionally within a range of wavelengths, emitted by the first light source. The first light source may emit light of various wavelengths across a wavelength band. It will be understood that the second wavelength is typically a peak or central wavelength, optionally within a range of wavelength, emitted by the second light source. The second light source may emit light of various wavelengths across a wavelength band.

By stating that the (e.g. at least one) detected light signal is indicative separately of detection (e.g. by the or each of the one or more photodetectors) of light of the first wavelength and light of the second wavelength, this will be understood to mean that the (e.g. at least one) detected light signal is such that detection of light of the first wavelength can be determined independently from detection of light of the second wavelength.

The (e.g. at least one) detected light signal may comprise a first detected light signal, optionally indicative of detection of light of the first wavelength. The (e.g. at least one) detected light signal may comprise a second detected light signal, optionally indicative of detection of light of the second wavelength. The (e.g. at least one) detected light signal may comprise a third detected light signal, optionally indicative of detection of light of the third wavelength.

A unit as described above that comprises one or more photodetectors, each configured to detect light reflected from within the upper arm when the unit is worn on the upper arm can be worn on the upper arm continuously and can therefore regularly output an indicator of blood oxygen saturation of blood in the upper arm. Such a unit can therefore be used to determine and optionally to monitor an indicator of blood oxygen saturation and in some cases to monitor blood oxygen saturation, as well as changes therein, over a period of time. This information is helpful to subjects and to health care professionals, allowing them to make better-informed decisions about subject healthcare.

The indicator of blood oxygen saturation may be an indicator of oxygen saturation in peripheral arterial blood ($SpO_2$). The indicator of blood oxygen saturation may be an indicator of the proportion of light of the first wavelength that was absorbed by the blood and tissues within the upper arm. The indicator of blood oxygen saturation may be an indicator of the proportion of light of the first wavelength that was reflected by the blood and tissues within the upper arm. The indicator of blood oxygen saturation may be an indicator of the proportion of light of the second wavelength that was absorbed by the blood and tissues within the upper arm. The indicator of blood oxygen saturation may be an indicator of the proportion of light of the second wavelength that was reflected by the blood and tissues within the upper arm. The indicator of blood oxygen saturation may be an indicator of a comparison of the proportion of light of the first wavelength that was absorbed by the blood and tissues within the upper arm to the proportion of light of the second wavelength that was absorbed by the blood and tissues within the upper arm. The indicator of blood oxygen saturation may be an indicator of a comparison of the proportion of light of the first wavelength that was reflected by the blood and tissues within the upper arm to the proportion of light of the second wavelength that was reflected by the blood and tissues within the upper arm. It will be understood that an indicator of a metric may be provided by a determined value of the metric itself. For example, the indicator of blood oxygen saturation may be a determined value of blood oxygen saturation.

It will be understood that light reflected from within the upper arm is light reflected from blood and/or tissues within the upper arm. It will be understood that reflected light is light that is reflected back towards the unit and not, for example, light that is scattered by blood and/or tissues within the upper arm but which, despite scattering, passes completely through the upper arm.

The unit may comprise a housing, the housing comprising an arm-facing portion having an incurvate surface for facing the upper arm. The unit may be configured such that at least part of the incurvate surface may contact the upper arm when the unit is worn on the upper arm. The arm-facing portion may comprise a sensitive region protruding from the incurvate surface. The unit may be configured such that when the unit is worn on the upper arm at least part of the sensitive region contacts the upper arm. For example, the incurvate surface and/or the sensitive region may be arranged such that at least part of the incurvate surface and at least part of the sensitive region contacts the upper arm when the unit is worn on the upper arm. The sensitive region may contact an area of the surface of the upper arm (for example, an area having a similar size and shape as the size and shape of the sensitive region) when the unit is worn on the upper arm.

The incurvate surface may have a degree of curvature of at least 30 degrees, or at least 50 degrees, or at least 60 degrees. The incurvate surface may have a degree of curvature of up to 110 degrees, or up to 90 degrees, or up to 80 degrees. For example, the incurvate surface may have a degree of curvature of between 60 degrees and 80 degrees, or between 65 degrees and 75 degrees, for example approximately 70 degrees.

The incurvate surface may be configured to curve around at least a part of the upper arm such that at least part of the sensitive region contacts the upper arm when the unit is worn on the upper arm. For example, the incurvate surface may be configured to curve around a lateral part of the upper arm between the shoulder and the elbow such that at least part of the sensitive region contacts a lateral part of the upper arm between the shoulder and the elbow when the unit is worn on the upper arm. However, it will be understood that the incurvate surface may be curved in such a way that it will also curve around other parts of the upper arm such that at least part of the sensitive region contacts the upper arm when the unit is worn on the upper arm. For example, if the unit is moved by the subject (i.e. to be positioned closer to or further from the shoulder and/or to be positioned at various locations around the perimeter of the upper arm, such as over the bicep or triceps, or at an inner part of the upper arm), and that the sensitive region will then contact at least part of the upper arm which the incurvate surface curves around when the unit is worn on the upper arm. The incurvate surface may have an irregular parabolic shape. It may be that a first cross-section through the incurvate surface in a first plane defines a first radius of curvature, and a second cross-section through the incurvate surface in a second plane, transverse to the first plane, defines a second radius of curvature, different to the first radius of curvature. The second plane may be parallel to an along-arm direction of the upper arm where the unit is to be worn on the upper arm. It may be that the second radius of curvature is less curved than the first radius of curvature. In other words, it may be that the incurvate surface wraps around at least a portion of the arm. The incurvate surface may be generally saddle-shaped.

The first and second light sources and the one or more photodetectors may be exposed to the upper arm (e.g. to the area of the surface of the upper arm) at the sensitive region, being arranged such that light can pass from the first and second light sources into the upper arm, and light can be received by the one or more photodetectors from within the upper arm when the unit is worn on the upper arm. The sensitive region may comprise (e.g. contain) the first and second light sources. The sensitive region may comprise (e.g. contain) the one or more photodetectors. The sensitive region may comprise (e.g. contain) the first and second light sources, arranged such that light can pass from the first and second light sources into the upper arm and light can be received by the one or more photodetectors from within the upper arm when the unit is worn on the upper arm.

The sensitive region may extend from the incurvate surface by at least 0.5 millimetres, or by at least 1 millimetre, or by at least 2 millimetres. The sensitive region my extend from the incurvate surface by no more than 6 millimetres, or by no more than 5 millimetres.

The housing may comprise a second surface for facing away from the upper arm when the unit is worn on the upper arm. The second surface may be substantially flat (e.g. without curvature) however this is not required, and the second surface may be curved. The housing may comprise one or more side walls extending between the incurvate surface and the second surface. The second surface may comprise a recessed portion. The second surface (optionally the recessed portion of the second surface) may comprise a power terminal. The second surface may comprise a user interface.

The arm-facing portion and/or the sensitive region may further comprise a ledge portion which protrudes further from the incurvate surface than the sensitive region protrudes from the incurvate surface. The ledge portion may be a ring-shaped ledge which surrounds the sensitive region. The ledge portion may be positioned between the sensitive region and an outer perimeter of the incurvate surface (e.g. where the incurvate surface meets a different surface of the unit, such as a side wall). The ledge portion may be configured to restrict the pressure that can be applied (e.g. by the sensitive region) to the upper arm. Advantageously, because the ledge portion protrudes further from the incurvate surface than the sensitive region protrudes from the incurvate surface, the ledge portion restricts the pressure that can be applied on the upper arm by the sensitive region, for example if the strap is too tight.

Because the unit has a housing comprising an arm-facing portion having an incurvate surface for facing the upper arm, the unit is comfortable for wearing on the upper arm because the curvature of this surface complements the convex curvature of the upper arm. Furthermore, the curvature of the incurvate surface means that the unit can be more stably located on the upper arm than would be the case if the surface were not incurvate. The unit is therefore less likely to rock or otherwise move around on the arm as the subject moves. The improves the reliability of the detected light signal and thus the determined indicator of blood oxygen saturation, because when the unit is allowed to move relative to the upper arm this can lead to artifacts in the signal due to, for example, backscatter of light from the first and second light sources and/or due to incoming light from other external light sources.

The housing may comprise plastics material. The housing may comprise a high thermal insulation plastics material. The housing may comprise a high optical insulation plastics material.

Because the sensitive region protrudes from the incurvate surface, better contact between the sensitive region and the upper arm can be achieved than would be the case if the sensitive region did not so protrude. As a result, it is less likely that there will be a gap between the sensitive region and the upper arm and therefore light will pass directly from the sensitive region into the upper arm (and correspondingly, reflected light from within the upper arm will pass directly from the upper arm to the one or more photodetectors). This also improves the reliability of the detected light signal because where light does not pass directly (or passes less directly) into the upper arm, noise will be introduced into the detected light signal due to backscatter.

The unit may be a unit configured for wearing on the arm, for example, on the upper arm. The unit may be configured for wearing on (e.g. around) the upper arm at the lateral side of the upper arm. The unit may be configured for wearing on the upper arm between the elbow and the shoulder. The lateral side of the upper arm will be understood to be the outer side of the upper arm, in that it is a side further from the median plane of the body than the inner side of the upper arm. The lateral side of the upper arm will be understood to be opposite to the inner side of the upper arm, between the anterior of the upper arm and the posterior of the upper arm.

A unit that is configured for wearing on the upper arm and particularly on the lateral side of the upper arm between the elbow and the shoulder is particularly effective for determining an indicator of blood oxygen saturation of blood in the upper arm of the subject wearing the unit. This is because the unit can be reliably and stably coupled against the upper arm so that the light signals are less likely to include artifacts due to motion or backscatter. In addition, the upper arm cannot be moved far from the torso which also means that the light signals are less likely to include artifacts due to motion than would be the case if the unit were configured for wearing around the wrist, for example.

Furthermore, unlike other sites such as the wrist, the upper arm contains relatively few veins near the surface of the skin but still typically has good blood perfusion. Where reflected light is received from within veins this can lead to less reliable light signals because veins contain blood with lower oxygen saturation. Where the unit is positioned over a vein this can also cause pulse wave artefacts due to venous pulsation, and such artefacts can appear similar to the light signal of a unit that is positioned such that it is not over a vein. Such false signals can be difficult to detect and difficult to remove with data processing and can therefore result in the output of an indicator of blood oxygen saturation that is misleading. Accordingly, a unit that is configured for wearing on the upper arm is safer for use in clinical settings, particularly where decisions about subject health care may be made in dependence on the indicator of blood oxygen saturation.

Circulation in the upper arm is also generally reliable in most populations. In contrast, circulation at the extremities (e.g. at the fingertip) can be significantly reduced due to various health conditions and due to low temperatures.

The upper arm is also a relatively comfortable site. Most subjects can reach their own upper arm easily and so can apply and remove the unit themselves. The upper arm is also convenient for healthcare professionals to reach, in order to help a subject to apply or remove the unit, or to check that the unit has been correctly positioned. Once the unit is on the upper arm it is out of the way of the subject and does not require the subject to move or behave in a modified way in order to keep the unit in position. There is typically no need to remove any hair or prepare the skin where the unit is worn on the upper arm.

The unit may comprise a motion sensor configured to output a detected motion signal indicative of motion of the unit. The motion sensor may comprise (e.g. be) an accelerometer. The detected motion signal may be indicative of translational motion. The motion sensor may comprise (e.g. be) a gyroscope. The detected motion signal may be indicative of rotational motion. The indicator of blood oxygen saturation may be determined in dependence on the detected motion signal. The one or more processors and memory including instructions may, when executed by the one or more processors, cause the apparatus to determine an indicator of blood oxygen saturation of blood in the upper arm in dependence on the (e.g. at least one) detected light signal and the detected motion signal. The one or more processors and memory including instructions may, when executed by the one or more processes, cause the apparatus to output the indicator of blood oxygen saturation in dependence on the detected motion signal.

The detected motion signal may be a motion signal that is indicative of motion of the unit, e.g. across a measurement period. The detected motion signal may be a motion signal that is indicative of motion of an upper arm, e.g. across a measurement period. The instructions may, when executed by the one or more processors, cause the apparatus to compare the motion signal to a predetermined threshold, where the predetermined threshold is indicative of a high degree of motion. The instructions may, when executed by the one or more processors, cause the apparatus to output the indicator of blood oxygen saturation in dependence on the detected motion signal only if the motion signal is below a predetermined threshold, where the predetermined threshold is indicative of a high degree motion. It will be understood that a high degree of motion is enough motion to lead to an unreliable indicator of blood oxygen saturation. The skilled person will appreciate that the determination of whether an indicator of blood oxygen saturation is unreliable will depend on various factors, including the use case and the calibration of the unit, for example.

The instructions may, when executed by the one or more processors, cause the apparatus to compare the motion signal to the (e.g. at least one) detected light signal to thereby determine a degree of correlation between the (e.g. at least one) detected light signal and the detected motion signal. The instructions may, when executed by the one or more processors, cause the apparatus to output an alert if the degree of correlation between the (e.g. at least one) detected light signal and the detected motion signal is above a predetermined threshold. For example, the predetermined threshold may be a threshold that is indicative of a degree of correlation indicative of a Pearson correlation coefficient above 0.25, or above 0.3 or above 0.4. The predetermined threshold is typically a threshold that is indicative of a degree of correlation indicative of a Pearson correlation coefficient of no more than 0.5.

Advantageously, a unit comprising a motion sensor can be used to determine whether the (e.g. at least one) detected light signal are suitable for use in determining the indicator of blood oxygen saturation. Similarly, a unit comprising a motion sensor can be used to determine whether the determined indicator of blood oxygen saturation is reliable or not. For example, the first and second light signals and/or the determined indicator of blood oxygen saturation may be unreliable or inaccurate where the subject is moving too much. Where a motion sensor is included in the unit, data coinciding with periods of relatively high motion (i.e. sufficient motion to cause the first and second light signals to be unreliable or inaccurate) can be rejected, and only data coinciding with relatively low motion can be selected for use in determining the indicator of blood oxygen saturation.

An accelerometer can be used to detect translational motion of the upper arm because the upper arm can only move a limited distance relative to the body and therefore movement of the upper arm leads to acceleration and deceleration within a short time period. A gyroscope can be used to detect rotational motion around an axis. Advantageously, a gyroscope does not need to be calibrated to take into account the effects of a gravitational field or local gravitational field changes.

The unit may comprise a plurality of accelerometers. For example, the unit may comprise two accelerometers or three accelerometers. The unit may comprise a plurality of gyroscopes. For example, the unit may comprise two gyroscopes or three gyroscopes. Where a plurality of accelerometers is provided, each accelerometer is typically configured to detect translational motion across an axis that is not parallel with the axis across which each other accelerometer is configured to detect translational motion. Alternatively, the unit may comprise a multi-axis (e.g. two-axis or three-axis) accelerometer. Similarly, where a plurality of gyroscopes is provided, each gyroscope is typically configured to detect rotational motion around an axis that is not parallel with the axis around which each other gyroscope is configured to detect rotational motion. In this way, motion of the upper arm may be determined in six degrees of freedom.

The processor may comprise a clock. The clock may be configured to provide a shared clock signal for sampling of both the detected motion signal and the (e.g. at least one) detected light signal.

By providing a shared clock signal for sampling of both the motion signal and the (e.g. at least one) detected light signal, the (e.g. at least one) detected light signal can be rejected and not used for determining an indicator of blood oxygen saturation when the motion signal is indicative of a level of motion which would lead to the indicator of blood oxygen saturation being inaccurate or unreliable. High levels of motion can lead to the unit rocking or moving on the arm which can lead to the determined indicator of blood oxygen saturation being inaccurate, e.g. due to backscatter. The skilled person will appreciate that a clock signal can also be helpful in data processing and analysis generally, as well as for calibration.

The apparatus may comprise a stabilising portion extending laterally from the unit and a securing means (e.g. a strap) extending from the stabilising portion, wherein the strap and stabilising portion are configured to hold the unit on the subject's upper arm. The strap may be more flexible than the stabilising portion. For example, the strap, stabilising portion, and unit may be integrally formed. However, this is not required and alternatively, the apparatus may comprise a securing means (e.g. a strap) to secure the apparatus at the upper arm. The strap may comprise: a unit receiving portion configured to releasably receive and retain the unit; a stabilising portion extending laterally from the unit receiving portion; and a flexible portion extending laterally from the unit receiving portion, wherein the strap is configured to hold the unit on the subject's upper arm. The flexible portion may be more flexible than the stabilising portion. The strap may comprise a fastener for fastening the strap around the upper arm. The stabilising portion may extend laterally from the unit via the unit receiving portion.

A strap is a convenient and comfortable way to hold the unit on the subject's upper arm. The subject or a healthcare professional can easily and intuitively apply and remove the unit via a strap, without the need for training or instructions.

Where a unit receiving portion is provided, rather than the unit being integrally formed in the strap, this allows the unit to be removed from the strap (e.g. for charging the unit or cleaning the strap).

The length of the strap may be at least 25 centimetres. The length of the strap may be at least 30 centimetres. The length of the strap may be at least 40 centimetres. Preferably, the strap is not longer than 70 centimetres. For example, the strap may be between 28 and 35 centimetres in length. The strap may be configured to surround an upper arm having a circumference of greater than 22 centimetres. The strap may be configured to surround an upper arm having a circumference of greater than 30 centimetres. For example, the strap may be configured to surround a circumference of between 23 and 32 centimetres.

Where a stabilising portion is provided, this helps to consistently couple the unit to the upper arm and limits the extent to which the unit can rock or otherwise move on the upper arm as the subject moves. The stabilising portion also mean that the unit is less likely to move if it is knocked (for example if the unit or the subject's upper arm contacts another object) and is less likely to be moved if the subject wears the unit whilst sleeping and moves during their sleep. The unit is also less likely to be moved by the movement of clothing (e.g. sleeves) against the unit or the arm. As a result, the light signals and consequently the determined indicator of blood oxygen saturation are more accurate and more reliable, as the signals are less likely to include artifacts due to movement of the unit.

The unit may be integrally formed in the strap. Alternatively, the unit (e.g. the incurvate surface) may be coated in an adhesive such that the unit may be held on the upper arm via the adhesive. Advantageously, where the unit is integrally formed with the strap, or where the unit is coated in an adhesive such that the unit may be held on the upper arm via the adhesive, the apparatus has fewer parts.

The strap may be resiliently deformable. At least a portion of the strap may be resiliently deformable. For example, it may be that at least a portion of the strap is resiliently deformable that the strap is configured to expand and contract in length in response to movement of the subject's upper arm when the unit is worn on the upper arm. The strap may comprise a resiliently deformable region. The strap may be elasticated.

A resiliently deformable strap is more comfortable on the subject's arm than a strap that is not resiliently deformable. This is because as the arm moves, the size of the perimeter which the strap must surround changes (due to expansion and contraction of muscles in the upper arm). A resiliently deformable strap can expand and contract in size to accommodate this change in size of the arm due to movement. Furthermore, a resiliently deformable strap holds the unit in place on the upper arm more reliably during movement.

The unit may be up to 5 centimetres wide. The unit may be up to 5 centimetres tall. The unit may be up to 3 centimetres deep. For example, the unit may be 4 centimetres tall, 4 centimetres wide and 2 centimetres deep. Typically, the unit is more than 1 centimetre wide. Typically, the unit is more than 1 centimetre tall. Typically, the unit is more than 0.2 centimetres deep. Accordingly, the unit is small enough that it can comfortably be worn on the upper arm without feeling cumbersome or unwieldy. The unit is small enough that it can be worn under sleeves.

The unit may be a unit configured for wearing by an adult. The unit may be a unit configured for wearing by a child. The unit may be a unit configured for wearing by an infant. The unit may be sized to cover no more than 3% of the surface of the upper arm, or no more than 5% of the surface of the upper arm, or no more than 8% of the surface of the upper arm. The unit preferable covers less than 15% of the surface of the upper arm, or less than 13% of the surface of the upper arm, or less than 10% of the surface of the upper arm.

Although typically the unit comprises first and second light sources, this need not be the case. The first and second light sources may, for example, be derived from a single light source. For example, the unit may comprise a (e.g. single) light source and one or more filters configured to allow a light of a first wavelength (e.g. a central or peak wavelength within a first band of wavelengths) and light of a second wavelength (e.g. a central or peak wavelength within a first band of wavelengths) to pass therethrough, wherein the second wavelength is different to the first wavelength. Optionally, the unit may comprise a light source and one or more filters configured to allow light of a first wavelength (e.g. a central or peak wavelength within a first band of wavelengths), light of a second wavelength (e.g. a central or peak wavelength within a first band of wavelengths), and further optionally light of a third wavelength (e.g. a central or peak wavelength within a first band of wavelengths) to pass therethrough, wherein the first, second, and third wavelengths are different wavelengths to each other.

The first light source may comprise a light emitting diode (LED). The first light source may comprise an array of LEDs. The first light source may be configured to emit red light. The first light source may comprise a filter which allows red light to pass therethrough. The first light source may emit light of a red wavelength, where a red wavelength will be understood to be a wavelength of between 600 and 750 nanometres.

The second light source may comprise an LED. The second light source may comprise an array of LEDs. The second light source may be configured to emit infrared light. The second light source may comprise a filter which allows infrared light to pass therethrough. The second light source may be configured to emit light of a wavelength, where an infrared wavelength will be understood to be a wavelength of between 850 and 1,000 nanometres.

Red and infrared wavelengths are reflected and absorbed differently by oxygenated and deoxygenated blood components and particularly by haemoglobin. Accordingly, by providing a light source configured to emit red light and a light source configured to emit infrared light, and by providing one or more photodetectors configured to detect light of the first (e.g. red) wavelength and light of the second (e.g.

infrared) wavelength, it is possible to determine how much of the light of each wavelength is reflected back to the one or more photodetectors and therefore how much of the light of each wavelength is absorbed by the blood and tissues in the upper arm. From this information, an indicator of blood oxygen saturation may be determined.

The unit may comprise a third light source configured to direct light of a third wavelength towards the upper arm when the unit is worn on the upper arm. The third wavelength may be different to the first wavelength. The third wavelength may be different to the second wavelength. The third light source may comprise an LED. The third light source may comprise an array of LEDs. The third light source may be configured to emit green light. The third light source may comprise a filter which allows green light to pass therethrough. The third light source may be configured to emit light of a green wavelength, where a green wavelength will be understood to be a wavelength of between 480 and 570 nanometres.

The (e.g. at least one) detected light signal indicative separately of detection (e.g. by the or each of the one or more photodetectors) of light of the first wavelength and light of the second wavelength may also be indicative separately of detection (e.g. by the or each of the one or more photodetectors) of light of the third wavelength. The (e.g. at least one) detected light signal may comprise a first wavelength signal component.

The (e.g. at least one) detected light signal may comprise a second wavelength signal component. The (e.g. at least one) detected light signal may comprise a third wavelength signal component.

The or each photodetector may be a light sensor. The or each photodetector may comprise a photodiode. The photodetector may be a plurality of photodetectors. The plurality of photodetectors may be a plurality of photodiodes. The plurality of photodetectors may be an array of photodetectors. At least one of the plurality of photodetectors may be configured to detect light having a different wavelength to the light configured to be detected by at least one other of the plurality of photodetectors. The plurality of photodetectors may comprise at least as many photodetectors are there are light sources configured to emit light of different wavelengths. The or each (e.g. at least one) photodetector may be configured to detect light of a red wavelength. The or each (e.g. at least one) photodetector may be configured to detect light of an infrared wavelength. The or each (e.g. at least one) photodetector may be configured to detect light of a green wavelength. The or each photodetector may comprise a charged coupled device. The photodetector may comprise a camera. The or each photodetector may comprise one or more filters. For example, the or each photodetector may comprise a filter which allows the first wavelength and/or the second wavelength and/or the third wavelength to pass therethrough.

The unit may comprise a temperature sensor configured to output a temperature signal indicative of the temperature of the subject's upper arm when the unit is worn on the subject's upper arm. The temperature sensor may comprise a thermometer.

Where the subject is cold, vasoconstriction can lead to less accurate or less reliable light signals and thus a less accurate or less reliable determined blood oxygen indicator. As such, a unit including a temperature sensor configured to measure the temperature of the subject's upper arm when the unit is worn on the subject's upper arm can be helpful because this measured temperature can be used in making a decision as to whether to reject a determined blood oxygen indicator that may be inaccurate due to low temperature of the subject. Alternatively or additionally, the measured temperature can be used to trigger an alert, to tell the subject to take an action to increase their temperature (for example, to put on an extra layer of clothing or to move indoors) so that more reliable or accurate light signals may be recorded, and a more reliable or accurate indicator of blood oxygen saturation can be determined.

Accordingly, the memory may include instructions, which when executed by the one or more processors, may cause the apparatus to generate an alert if the temperature signal is indicative of a temperature below a predetermined threshold temperature, when the instructions are executed by the one or more processors. The alert may be an alert to prompt the subject to take action to increase their temperature. The predetermined threshold temperature may be a temperature below 35° C., or below 32° C., or below 30° C. The predetermined threshold temperature is typically above 25° C., or above 28° C.

The unit may comprise an (e.g. internal) power source. The power source may be a battery. The power source may be a rechargeable battery. The unit (e.g. the housing of the unit) may comprise a power terminal (e.g. three terminals) configured to allow charging of the power source (e.g. the battery). The housing of the unit may comprise a power terminal configured to allow charging of the power source (e.g. the battery) on a surface of the housing other than the incurvate surface. For example, the housing of the unit may comprise a power terminal configured to allow charging of the power source (e.g. the battery) on a surface of the housing opposite to the incurvate surface which faces away from the subject's upper arm when the unit is worn on the subject's upper arm, for example the second surface. Advantageously, by positioning a power terminal on a surface other than the incurvate surface, it is possible to charge the power source of the unit without first removing the unit from the upper arm.

The apparatus may comprise a charger configured to charge the power source (e.g. the battery) of the unit via the power terminal. The charger may comprise a power cable and a terminal connector configured to reversibly connect to the power terminal. Where a power cable is provided, this means that the unit can be charged without the unit first needing to be removed from the upper arm of the subject. The power cable may be at least 1 meter in length, or at least 2 meters in length, or at least 5 meters in length. Preferably the power cable is less than 10 meters in length. The terminal connector may be configured to reversibly connect to the power terminal magnetically. The terminal connector may be configured to reversibly connect to the power terminal via one or more clips.

According to a further aspect of the invention, there is provided a method of monitoring blood oxygen saturation of a subject, using an apparatus for monitoring blood oxygen saturation of a subject, the apparatus comprising a unit configured for wearing, the unit comprising:

a first light source configured to direct light of a first wavelength towards the upper arm when the unit is worn on the upper arm;

a second light source configured to direct light of a second wavelength towards the upper arm when the unit is worn on the upper arm, the second wavelength being different to the first wavelength; and one or more photodetectors, each configured to output a (e.g. at least one) detected light signal indicative separately of detection (e.g. by the or each of the one or more photodetectors) of light of the first wavelength and light of the second wavelength reflected from within the upper arm when the unit is worn on the upper arm, wherein the apparatus comprises one or more processors and a memory including instructions which, when executed by the one or more processors, causes the apparatus to:

determine an indicator of blood oxygen saturation of blood in the upper arm in dependence on the (e.g. at least one) detected light signal; and output the indicator of blood oxygen saturation, the method comprising:

causing the first and second light sources to direct light towards the upper arm;

causing the one or more photodetectors to detect reflected light and to thereby output at least one detected light signal indicative separately of detection (e.g. by the or each of the one or more photodetectors) of light of the first wavelength and light of the second wavelength reflected from within the upper arm; and.

processing the (e.g. at least one) detected light signal to thereby determine an indicator of blood oxygen saturation of blood in the upper arm.

The method may comprise outputting the determined indicator of blood oxygen saturation.

The method may comprise locating the unit on the upper arm. The method may comprise causing the subject to wear the unit on the upper arm. The method may comprise holding the unit on the upper arm, for example with a strap.

A method of monitoring blood oxygen saturation of a subject using an apparatus as described above that comprises one or more photodetectors configured to detect light reflected from within the upper arm when the unit is worn on the upper arm can be used to regularly determine an indicator of blood oxygen saturation. Such a method can therefore be used to monitor an indicator of blood oxygen saturation and to thereby monitor blood oxygen saturation, as well as changes therein. This information is helpful to subjects and to health care professionals, allowing them to make better-informed decisions about subject healthcare.

The method may comprise processing the determined indicator of blood oxygen saturation of blood in the upper arm to determine an estimate of blood oxygen saturation of the subject. The method may comprise outputting the determined estimate of blood oxygen saturation of the subject.

The skilled person will appreciate that there may be a variety of indicators of blood oxygen saturation which may be determined according to the invention. Depending on the indicator of blood oxygen saturation to be determined, the steps in the method of processing the indicator of blood oxygen saturation may vary. Advantageously, a method that comprises processing the determined indicator of blood oxygen saturation to determine an estimate of blood oxygen saturation and outputting the estimate of blood oxygen saturation means that a physiological parameter is output rather than a proxy for the physiological parameter, and this parameter can be used to make decisions about subject healthcare, for example.

The method may comprise processing the motion signal to determine whether the subject is moving enough to cause the first and/or second light signals to be unsuitable for use in determining an indicator of blood oxygen saturation. Processing the motion signal may take place prior to determining an indicator of blood oxygen saturation and/or prior to outputting a determined indicator of blood oxygen saturation. For example, the method may comprise processing the at least one motion signal to determine whether the subject is moving enough to cause artifacts in the first and/or second light signals. The method may comprise rejecting the first and second light signals and not determining an indicator of blood oxygen saturation where it has been determined that the subject is moving enough to cause artifacts in the first and/or second light signals. The method may comprise not outputting the determined indicator of blood oxygen saturation where it has been determined that the subject is moving enough to cause artifacts in the first and/or second light signals.

The method may comprise processing the detected motion signal to determine whether the subject is moving enough to cause the determined indicator of blood oxygen saturation to be unreliable. The method may comprise processing the (e.g. at least one) detected light signal to determine whether the subject is moving enough to cause the determined estimate of blood oxygen saturation to be unreliable. The method may comprise outputting the determined indicator of blood oxygen saturation in dependence on whether the calculated estimate of blood oxygen saturation of the subject is determined to be unreliable.

Processing the detected motion signal may comprise determining whether the detected motion signal is above a predetermined threshold that is indicative of high motion. Processing the (e.g. at least one) detected light signal may comprise dividing the (e.g. at least one) detected light signal into a series of windows of detected light signal data across a measurement period. Processing the detected light signal data may comprise comparing the windows of detected light signal data across the measurement period. Processing the detected light signal data may comprise determining a distribution of the detected light signal data (or data derived therefrom), e.g. across the measurement period. Processing the (e.g. at least one) detected light signal may comprise compiling a histogram of the light signal data in the series of windows of detected light signal data. Processing the (e.g. at least one) detected light signal may comprise determining the distribution of the histogram of the detected light signal data. The measurement period may be a period of at least 3 seconds, preferably at least 5 seconds, more preferably at least 8 seconds. The measurement period is preferably less than 60 seconds, preferably less than 30 seconds, preferably less than 25 seconds.

The method may comprise determining the distribution of the detected light signal data (or data derived therefrom) by comparing a frequency-dependent component of the first wavelength signal to a frequency-independent component of the first wavelength signal (e.g. by determining a first ratio of the frequency-dependent component of the first wavelength signal to the frequency-independent component of the first wavelength signal) for each window of detected light signal data across the measurement period. The method may comprise determining the distribution of the detected light signal data (or data derived therefrom) by comparing a frequency-dependent component of the second wavelength signal to a frequency-independent component of the second wavelength signal (e.g. by determining a second ratio of the frequency-dependent component of the second wavelength signal to the frequency-independent component of the second wavelength signal) for each window of detected light signal data across the measurement period. The method may comprise comparing the first ratio to the second ratio (e.g. by determining a ratio of the first ratio to the second ratio) for each window of detected light signal data across the measurement period. The distribution of the detected light signal data (or data derived therefrom) may comprise a ratio of the first ratio to the second ratio for each window of detected light signal data across the measurement period.

The method may comprise determining the distribution of the histogram of detected light signal data (or information derived therefrom) by comparing a frequency-dependent component of the first wavelength signal to a frequency-independent component of the first wavelength signal (e.g. by determining a first ratio of the frequency-dependent component of the first wavelength signal to the frequency-independent component of the first wavelength signal) for each window of detected light signal data across the measurement period. The method may comprise determining the distribution of the histogram of detected light signal data by comparing a frequency-dependent component of the second wavelength signal to a frequency-independent component of the second wavelength signal (e.g. by determining a second ratio of the frequency-dependent component of the second wavelength signal to the frequency-independent component of the second wavelength signal) for each window of detected light signal data across the measurement period. The method may comprise comparing the first ratio to the second ratio (e.g. by determining a ratio of the first ratio to the second ratio) for each window of detected light signal data across the measurement period. The histogram of the detected light signal data may comprise a ratio of the first ratio to the second ratio for each window of detected light signal data across the measurement period.

Where the detected light signal data, data derived therefrom, and/or a histogram of detected light signal data has a narrow distribution, this may be indicative of a low level of movement. Accordingly, where the detected light signal data, data derived therefrom, and/or a histogram of detected light signal data has a narrow distribution, this can be used as an indicator that the calculated estimate of blood oxygen saturation is not unreliable. Conversely, where the detected light signal data, data derived therefrom, and/or a histogram of detected light signal data has a broad distribution, this may be indicative of a high level of movement and thus an indicator that the calculated estimate of blood oxygen saturation is reliable. The method may comprise comparing the distribution of the detected signal light signal data, data derived therefrom, and/or the histogram of detected light signal data to calibration data to determine whether the said distribution meets predetermined criteria, wherein if the predetermined criteria are met, the distribution will be regarded as narrow.

The method may comprise determining a device-specific (e.g. linear) calibration function. The method may comprise comparing the ratio of the first ratio to the second ratio for each window of detected light signal data across the measurement period to the device-specific (e.g. linear) calibration function to determine an indicator of blood oxygen saturation. For example, the indicator of blood oxygen saturation may be an estimate of blood oxygen saturation.

The method may comprise determining how much the indicator of blood oxygen saturation varies across a measurement period. The method may comprise outputting the estimate of blood oxygen saturation only when the estimate is indicative of a change of less than ±5 percent (or percentage points) within a measurement period of 8 seconds, or a change of less than ±3 percent (or percentage points) within a measurement period of 8 seconds, or a change of less than ±2 percent (or percentage points) within a measurement period of 8 seconds, or a change of less than ±1 percent (or percentage points) within a measurement period of 8 seconds.

The method may comprise one or more further processing steps in dependence on whether the calculated estimate of blood oxygen saturation of the subject is determined to be unreliable. The method may comprise rejecting the determined indicator of blood oxygen saturation if the determined indicator is unreliable. The method may comprise outputting the determined indicator of blood oxygen saturation if (e.g. only if) the calculated estimate of blood oxygen saturation is determined to be not unreliable.

Because a high degree of motion of the subject (e.g. of the subject's upper arm) can cause movement of the unit relative to the upper arm, this can lead to artifacts in the first and second light signals, which in turn can lead to an inaccurate or unreliable determined indicator of blood oxygen saturation. By determining whether the subject is moving enough to cause the determined indicator of blood oxygen saturation to be unreliable and either not determining an indicator of blood oxygen saturation, or rejecting or not outputting the determined indicator of blood oxygen saturation where it is unreliable, the method is safer. This is because no decisions about subject healthcare are made on the basis of an unreliable indicator of blood oxygen saturation.

The method may comprise storing data from the first and/or second light signals and/or the motion signal for subsequent processing. The method may comprise processing the first and/or second light signals to remove artifacts, for example artifacts due to motion of the subject and/or the unit, and/or artifacts due to backscatter.

It should be understood that where the determined indicator of blood oxygen saturation is rejected this does not necessarily mean that the determined indicator of blood oxygen saturation is deleted or discarded. The determined indicator of blood oxygen saturation may be further processed or analysed and/or recorded for further processing or analysis. It may be that further processing or analysis data relating to a rejected determined indicator of blood oxygen saturation is still useful, even where it is not directly suitable for outputting. For example, rejected detected light signal data and/or motion signal data, and/or data relating to a determined indicator of blood oxygen saturation (e.g. of blood in the subject's upper arm) based on rejected detected light signal data may be used in improving processing techniques, or in developing improvements in the unit or apparatus.

The (e.g. at least one) detected light signal may comprise a first and second wavelength signal components, indicative of light of the first and second wavelengths received by the one or more photodetectors.

Processing the (e.g. at least one) detected light signal may comprise:

determining a frequency-dependent component of the first wavelength signal component;

determining a frequency-independent component of the first wavelength signal component; and determining a first ratio, where the first ratio is a ratio of the frequency-dependent component to the frequency-independent component of the first wavelength signal component.

Processing the (e.g. at least one) detected light signal may comprise:

determining a frequency-dependent component of the second wavelength signal component;

determining a frequency-independent component of the second wavelength signal component;

determining a second ratio, wherein the second ratio is a ratio of the frequency-dependent component to the frequency-independent component of the second wavelength signal component.

Processing the (e.g. at least one) detected light signal may determining the ratio of the first ratio to the second ratio. Processing the (e.g. at least one) detected light signal may comprise comparing the determined the ratio of the first ratio to the second ratio to a calibration data set to thereby determine an estimate of blood oxygen saturation.

Processing the frequency-dependent and frequency-independent components of the first and second wavelength signal components to determine the first and second ratios and determining the ratio of the first ratio to the second ratio is a particularly effective processing method for determining an indicator of blood oxygen saturation.

Processing the frequency-dependent and frequency-independent components of the first and second wavelength components may comprise taking a sample of detected light signal data corresponding to a time period. Processing the frequency-dependent and frequency-independent components of the first and second wavelength components may comprise taking a sample of motion signal data corresponding to a (e.g. the same) time period.

Processing the frequency-dependent and frequency-independent components of the first and second wavelength signal components may comprise comparing the frequency-dependent and frequency-independent components to a (e.g. device-specific, e.g. linear) calibration function. Processing the frequency-dependent and frequency-independent components of the first and second wavelength signal components may comprise comparing the ratio of the first ratio to the second ratio for each window of detected light signal data across the measurement period to the (e.g. device-specific, e.g. linear) calibration function to determine an indicator of blood oxygen saturation. For example, the indicator of blood oxygen saturation may be an estimate of blood oxygen saturation. The (e.g. device-specific, e.g. linear) calibration function may be derived by testing the device with healthy subjects and comparing the resulting determined indicator of blood oxygen saturation to a known blood oxygen saturation, e.g. as determined via a hypoxia test.

The frequency-dependent components of the first and second wavelength components may be components of the (e.g. at least one) detected light signal that vary generally sinusoidally as a function of time, for example within a window of data corresponding to a predetermined time period (e.g. 8 seconds). The frequency-independent components of the first and second wavelength components may be components of the (e.g. at least one) detected light signal that do not vary generally sinusoidally, or that vary in less than one complete cycle of any sinusoidal function, within a window of data corresponding to a predetermined time period (e.g. 8 seconds). Accordingly, the frequency-dependent components of the first and second wavelength components may be thought of as relatively high-frequency components expressible as sinusoidal functions where the sinusoidal functions repeat at least once in the predetermined time period and the frequency-independent components of the first and second wavelength components may be thought of as relatively low-frequency components which do not necessarily (and typically do not) have a sinusoidal component which repeats at least once in the predetermined time period.

The method may comprise comparing the (e.g. at least one) detected light signal to the detected motion signal to thereby determine a degree of correlation between the (e.g. at least one) detected light signal and the detected motion signal. The method may comprise generating an alert if the degree of correlation between the (e.g. at least one) detected light signal and the detected motion signal is above a predetermined threshold. For example, the predetermined threshold may be a threshold that is indicative of a degree of correlation indicative of a Pearson correlation coefficient above 0.25, or above 0.3 or above 0.4. The predetermined threshold is typically a threshold that is indicative of a degree of correlation indicative of a Pearson correlation coefficient of no more than 0.5.

The alert may be an alert to prompt the subject (or a user or a heath care professional) to reposition the unit (e.g. to reposition the unit on the upper arm). The alert may be an alert to prompt the subject (or a user or a health care professional) to tighten a (e.g. the) strap. The alert may be an alert to prompt the subject (or a user or a health care professional) to increase the temperature of the subject (e.g. by moving indoors or putting on an additional layer of clothing).

Where a unit according to the invention is poorly coupled to the upper arm, a false signal due to breathing motion can arise. By comparing the (e.g. at least one) detected light signal and the detected motion signal to determine a degree of correlation, it is possible to determine whether the such a false signal due to breathing motion has been generated. This is possible because the detected motion signal and the (e.g. at least one) detected light signal should not be correlated to each other. As such, this method can be used to improve the reliability of the indicator of blood oxygen saturation.

The method may comprise processing a temperature signal from a temperature sensor. Processing the temperature signal may take place prior to determining an indicator of blood oxygen saturation and/or prior to outputting a determined indicator of blood oxygen saturation. For example, the method may comprise processing the temperature signal to determine whether the subject is cold enough to cause reduced intensity in the first and/or second light signals to the extent that the resulting determined indicator of blood oxygen saturation would be unreliable or inaccurate. The method may comprise rejecting the first and second light signals and not determining an indicator of blood oxygen saturation where it has been determined that the subject is cold enough to cause reduced intensity in the first and/or second light signals to the extent that the resulting determined indicator of blood oxygen saturation would be unreliable or inaccurate (e.g. as a result of vasoconstriction). The method may comprise not outputting the determined indicator of blood oxygen saturation where it has been determined that the subject is cold enough to cause reduced intensity in the first and/or second light signals to the extent that the resulting determined indicator of blood oxygen saturation would be unreliable or inaccurate.

Where the temperature signal is indicative of a subject that is cold (e.g. where the temperature is determined to be below a predetermined value, for example below 32 1° C.), the method may comprise creating an alert and alerting the subject to their low temperature. The method may comprise prompting the subject to take action to raise their temperature. For example, the method may comprise prompting the subject to put on an extra layer of clothing. The method may comprise prompting the subject to move indoors.

The method may comprise only outputting a determined indicator of blood oxygen saturation when the temperature signal is not indicative of a subject that is cold (e.g. where the temperature is determined to not be below a predetermined value, or is determined to be above a predetermined value, for example above 32° C.). The method may comprise only determining an indicator of blood oxygen saturation when the temperature signal is not indicative of a subject that is cold (e.g. where the temperature is determined to not be below a predetermined value, or is determined to be above a predetermined value, for example above 32° C.).

The (e.g. at least one) detected light signal may comprise, first, second, and third wavelength signal components, indicative of light (e.g. light intensity, proportion of light, or another characteristic of light) of the respective wavelength received by the one or more photodetectors. The first wavelength may be a red wavelength. The second wavelength may be an infrared wavelength. The third wavelength may be a green wavelength.

The method may comprise causing the first, second, and optionally the third light sources to be switched on and off, e.g. in sequence. For example, the method may comprise:

causing the first light source to be switched on (and thus the method may comprise causing the first light source to direct light of the first wavelength towards to upper arm);

causing the first light source to be switched off (and thus may the method may comprise causing the first light source to stop directing light of the first wavelength towards the upper arm);

causing the second light source to be switched on (and thus the method may comprise causing the second light source to direct light of the second wavelength towards to upper arm);

causing the second light source to be switched off (and thus may the method may comprise causing the second light source to stop directing light of the second wavelength towards the upper arm);

causing the third light source to be switched on (and thus the method may comprise causing the third light source to direct light of the third wavelength towards to upper arm); and/or causing the third light source to be switched off (and thus may the method may comprise causing the third light source to stop directing light of the third wavelength towards the upper arm).

The method may comprise first causing the first light source to be switched on and then off, and then causing the second light source to be switched on and then off, and then optionally causing the third light source to be switched on and then off. However, the first, second and/or third light sources may be switched on and then off in a different order, or simultaneously. The first, second and/or third light sources may be switched on for the duration of a measurement period.

Switching the first, second and/or third light sources on and then off may happen at least 10 times per second, or at least 30 times per second, or at least 50 times per second, or at least 100 times per second. Switching the first, second, and/or third light sources on and then off may happen fewer than 1000 times per second.

The method may comprise comparing the first wavelength signal component to the third wavelength signal component to thereby determine a degree of correlation between the first wavelength signal component and the third wavelength signal component. Alternatively or additionally, the method may comprise comparing the second wavelength signal component to the third wavelength signal component thereby determine a degree of correlation between the second wavelength signal component and the third wavelength signal component. The method may comprise generating an alert if the degree of correlation between the first and/or second wavelength signal components and the third wavelength signal component is below a predetermined threshold. For example, the predetermined threshold may be a threshold that is indicative of a degree of correlation indicative of a Pearson correlation coefficient below 1, or above 0.5 or above 0.4. The predetermined threshold is typically a threshold that is indicative of a degree of correlation indicative of a Pearson correlation coefficient of at least than 0.3.

The alert may be an alert to prompt the subject (or a user or a heath care professional) to reposition the unit (e.g. to reposition the unit on the upper arm). The alert may be an alert to prompt the subject (or a user or a health care professional) to tighten a (e.g. the) strap. The alert may be an alert to prompt the subject (or a user or a health care professional) to loosen a (e.g. the) strap.

Where the unit is positioned over a vein, this can lead to an unreliable indicator of blood oxygen saturation of blood in the upper arm. This is both because positioning of the unit over a vein can lead to venous pulsation, creating noise in the (e.g. at least one) detected light signal, and also because veins contain less oxygen than arterial blood. Therefore, if light is reflected from within veins and is detected by one or more of the one or more photodetectors, this can lead to an indicator of blood oxygen saturation that is falsely low. Green wavelengths do not penetrate as far into the arm as light of red to infrared wavelengths, and therefore green light rarely penetrates deep enough into the arm for it to impinge on venous blood. As a result, light of green wavelengths reflected from within the upper arm (and thus the third wavelength signal component) is unlikely to have been reflected from blood in a vein and is unlikely include any venous pulsation signal artefacts. In contrast, where the unit is placed over a vein, the first and second wavelength signal components are more likely to include venous pulsation signal artefacts. Therefore, if the first and second wavelength signal components do not strongly correlate with the third signal component, this can be indicative of a unit that has been incorrectly placed over a vein. By generating an alert when this occurs, to prompt the unit to be moved, the output of an unreliable indicator of blood oxygen saturation can be avoided.

Accordingly, the method may comprise comparing the first and/or second wavelength signal components to the third wavelength signal component to thereby determine a degree of correlation between the first and/or second wavelength signal components and the third wavelength signal component. The method may comprise generating an alert when the degree of correlation between the first and/or second wavelength signal components and the third wavelength signal component is below a predetermined correlation threshold. The method may comprise determining a vein correlation parameter indicative of light from the first wavelength and/or light of the second wavelength being reflected from a vein in the upper arm. The vein correlation parameter may be determined in dependence on the comparison between the first and/or second wavelength signal components to the third signal component. The method may comprise detecting a vein, e.g. by comparing the first and/or second wavelength signal components to the third wavelength signal component and determining that the degree of correlation between the first and/or second wavelength signal components and the third wavelength signal component is below a predetermined correlation threshold.

The method may comprise creating one or more alerts. For example, the method may comprise creating an alert to prompt the subject or a healthcare professional to take an action. The method may comprise creating an alert to prompt the user to do one or more of the following:
    reposition the device;
    tighten or loosen the strap;
    loosen the strap;
    reduce movement by the subject;
    increase the subject's temperature.

The method may comprise creating one or more alerts in dependence on a received signal. The received signal may be one or more of:
    a (e.g. at least one of the at least one) detected light signal;
    a (e.g. the) motion signal;
    a (e.g. the) temperature signal.

The method my comprise calibration of the unit. The method may comprise calibration of the (e.g. at least one) detected light signal. The method may comprise calibration of the detected motion signal. The method may comprise calibration of the detected temperature signal.

The method may comprise periodic recalibration of the (e.g. at least one) detected light signal. For example, the method may comprise calibration of the (e.g. at least one) detected light signal at least once every hour, preferably at least once every five minutes, more preferably at least once every 5 seconds. The method typically comprises calibration of the (e.g. at least one) detected light signal no more than once every second. The (e.g. at least one) detected light signal during calibration is typically not used in determining an indicator of blood oxygen saturation of blood in the upper arm. Any indicator of blood oxygen saturation detected during calibration is typically not output.

Calibration at least once every hour is helpful because the unit is typically worn on the subject's upper arm for at least several hours, and during this time the unit may move and/or the signal may change due to changes in blood flow in the upper arm (for example due to vasoconstriction or dilation as the subject's temperature varies). As such, by regularly calibrating (or re-calibrating) the (e.g. at least one) detected light signal, the quality of the signal is less likely to deteriorate over extended time periods.

The unit may comprise a power source (e.g. a battery) and the method may comprise charging the power source. The method may comprise charging the power source while the unit is worn on the upper arm. Alternatively, the method may comprise removing the unit from the upper arm and subsequently charging the power source.

The method may comprise suppressing the output of an indicator of blood oxygen saturation when an alert is generated.

According to a further aspect of the invention there is provided a kit of parts comprising: apparatus for monitoring blood oxygen saturation of a subject, the apparatus comprising a unit configured for wearing on the subject's upper arm, the unit comprising:
    a first light source configured to direct light of a first wavelength towards the upper arm when the unit is worn on the upper arm;
    a second light source configured to direct light of a second wavelength towards the upper arm when the unit is worn on the upper arm, the second wavelength being different to the first wavelength; and
    one or more photodetectors, each configured to output a (e.g. at least one) detected light signal indicative separately of detection (e.g. by the or each of the one or more photodetectors) of light of the first wavelength and light of the second wavelength reflected from within the upper arm when the unit is worn on the upper arm, wherein the apparatus comprises one or more processors and a memory including instructions; and a securing means (e.g. a strap) configured to hold the unit on the subject's upper arm; and The kit may comprise a power source (e.g. a battery, optionally a rechargeable battery). The kit may comprise a charger for charging the power source.

A kit comprising a unit, strap and charger as discussed above is a particularly convenient kit for a subject of healthcare professional to use to thereby determine an indicator of blood oxygen saturation (e.g. of blood in the upper arm), or an estimate of blood oxygen saturation. The subject and/or a healthcare professional can conveniently use such a kit for monitoring physiological parameters relating to and optionally including blood oxygen saturation, and for making healthcare decisions in dependence on the said physiological parameters.

The power source may be an internal power source. The power source may be a battery. The power source may be a rechargeable battery. The unit may comprise a power terminal configured for charging of the power source. The housing of the unit may comprise a power terminal configured to allow charging of the power source on a surface of the housing which is not configured to face the subject's upper arm when the unit is worn on the subject's upper arm. The charger may comprise a power cable and a terminal connector configured to reversibly connect to the power terminal.

The charger may thus be configured to allow charging of the power source without removing the unit from the upper arm of the subject. Alternatively or additionally, the charger may be configured to allow charging of the power source when the unit is not on the upper arm of the subject. The charger may be configured to allow charging of the power source without removing the power source from the unit.

In particular, where the unit includes a power source, and the kit includes a charger for the power source, the power source does not need to be replaced and can instead be recharged. Furthermore, when the power source is charged, the unit can be worn without the attachment of a power cable, thus allowing the subject to walk around more conveniently.

The apparatus or the kit may comprise a controller configured to carry out one or more of the steps of the method.

It will be understood that any features described above in relation to the unit according to any other aspect of the invention are optional features of the unit.

DESCRIPTION OF THE DRAWINGS

An example embodiment of the present invention will now be illustrated with reference to the following Figures in which:

FIG. 5a is a side elevation view diagram of an example of a unit according to the invention and FIGS. 5b and 5c are front and back elevation view diagrams of the example of FIG. 5a;

DETAILED DESCRIPTION OF AN EXAMPLE EMBODIMENT

Figure 1:
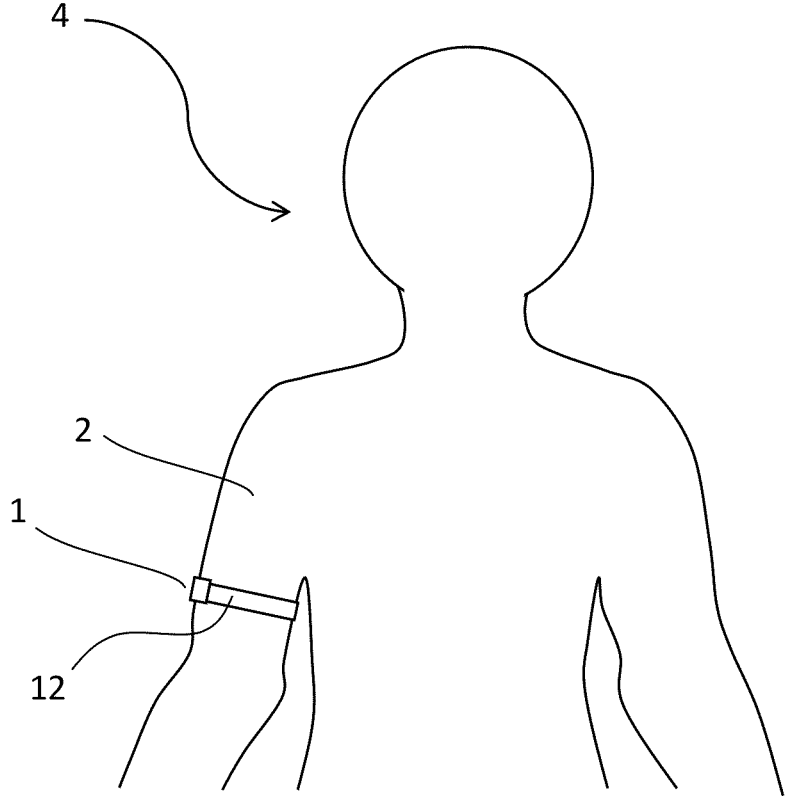
FIG. 1 is a diagram of an apparatus according to an example aspect of the invention, wherein the unit is held on the upper arm of a subject by a strap.

With reference to FIGS. 1 to 5c, the invention provides apparatus for monitoring the blood oxygen saturation of a subject 4. The apparatus includes a unit 1 for wearing on the upper arm 2 of a subject 4. The unit 1 is configured to determine an estimate of blood oxygen saturation, and specifically the level of oxygen saturated in peripheral arterial blood ($SpO_2$) of the upper arm 2. The unit 1 updates the determined estimate of blood oxygen saturation periodically, provided that the estimate meets a predetermined level of accuracy and reliability. The unit 1 continuously outputs the most recently determined estimate of blood oxygen saturation.

The unit 1 has a housing 6 with an arm facing portion having an incurvate surface 8 for facing the upper arm 2 of the subject 4 when the unit is worn on the upper arm 2. The arm-facing portion has a sensitive region 10 which protrudes from the incurvate surface 8. The housing 6 has a generally planar outer surface 46 opposite to the incurvate surface 8 which faces away from the upper arm 2 of the subject when the unit is worn on the upper arm 2. The housing 6 has a rounded outer perimeter wall 50 which extends between the incurvate surface 8 and the planar outer surface 46.

The housing 6 contains red, infrared, and green light sources in the form of a red light emitting diode (LED) 14A, an infrared LED 14B, and a green LED 14C, respectively.

The red, infrared, and green LEDs 14A, 14B, 14C are positioned in the sensitive region 10 in such a way as to allow light emitted from the LEDs to pass from the sensitive region 10 of the housing 6 and into the upper arm 2 when the unit 1 is worn on the upper arm. The green LED emits light having a central wavelength of 530 nanometres. The red LED emits light having a central wavelength of 660 nanometres. The infrared LED emits light having a central wavelength of 950 nanometres.

The sensitive region 10 of the housing 6 also holds a photosensor array 16 which includes first, second and third photosensors. The first photosensor is configured to detect light of red wavelengths, the second photosensor is configured to detect light of infrared wavelengths and the third photosensor is configured to detect light of green wavelengths. Here, the LEDs 14A, 14B, 14C and photosensor array 16 are directly beneath the surface of the sensitive region 10, being covered by transparent windows that are transparent to the wavelengths emitted by the LEDs 14a, 14B, 14C.

Within the housing 6 there are three gyroscopes 20A, 20B, 20C which measure rotation around three orthogonal axes. Each gyroscope 20A, 20B, 20C is formed by a three-axis solid state gyroscope device. The gyroscopes 20A, 20B, 20C are fixed in position within the casing with a known orientation and are calibrated during manufacture. An offset is determined for the gyroscopes 20A, 20B, 20C so that measurements can be obtained of rotation around an axis in either sense. Further references to gyroscope measurement data refer to calibrated measurements, after allowing for the gyroscope offset.

The housing 6 further also contains three accelerometers 21A, 21B, 21C which measure acceleration along three orthogonal axes, each accelerometer 21A, 21B, 210C being formed by a three-axis MEMS accelerometer device. The accelerometers 21A, 21B, 21C are fixed in position within the casing with a known orientation and are calibrated during manufacture. Accelerometer data is processed to remove the signal caused by gravity. Further references to accelerometer measurement data refer to the calibrated measurements, after allowing for the subtraction of gravity from the accelerometer signals.

The unit has a temperature sensor 42 in the form of a thermometer, positioned in the incurvate surface 8 and configured to determine the temperature of the subject 4.

Figure 3A:
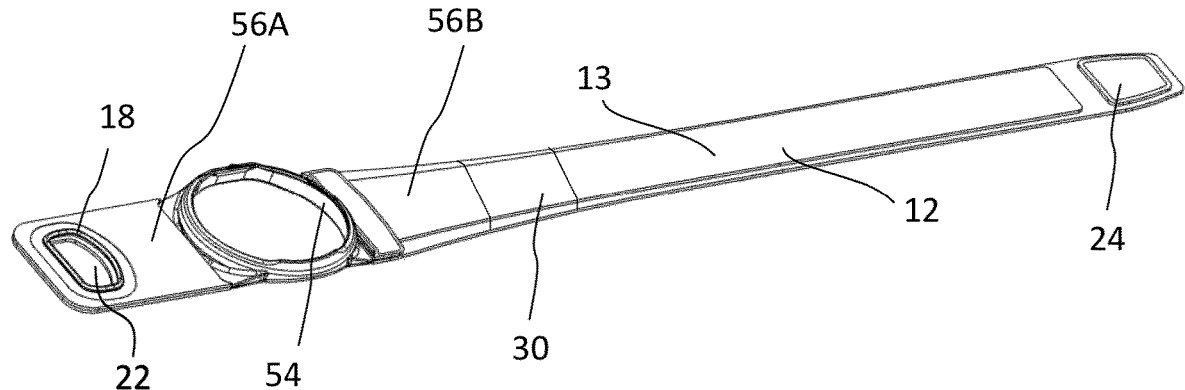
FIG. 3a is a perspective view diagram of a strap for a unit according to an example embodiment of the invention where the strap is laid flat and FIG. 3b is a perspective view diagram of the same strap, where the strap is positioned as it would be fastened around an upper arm.
Figure 3B:
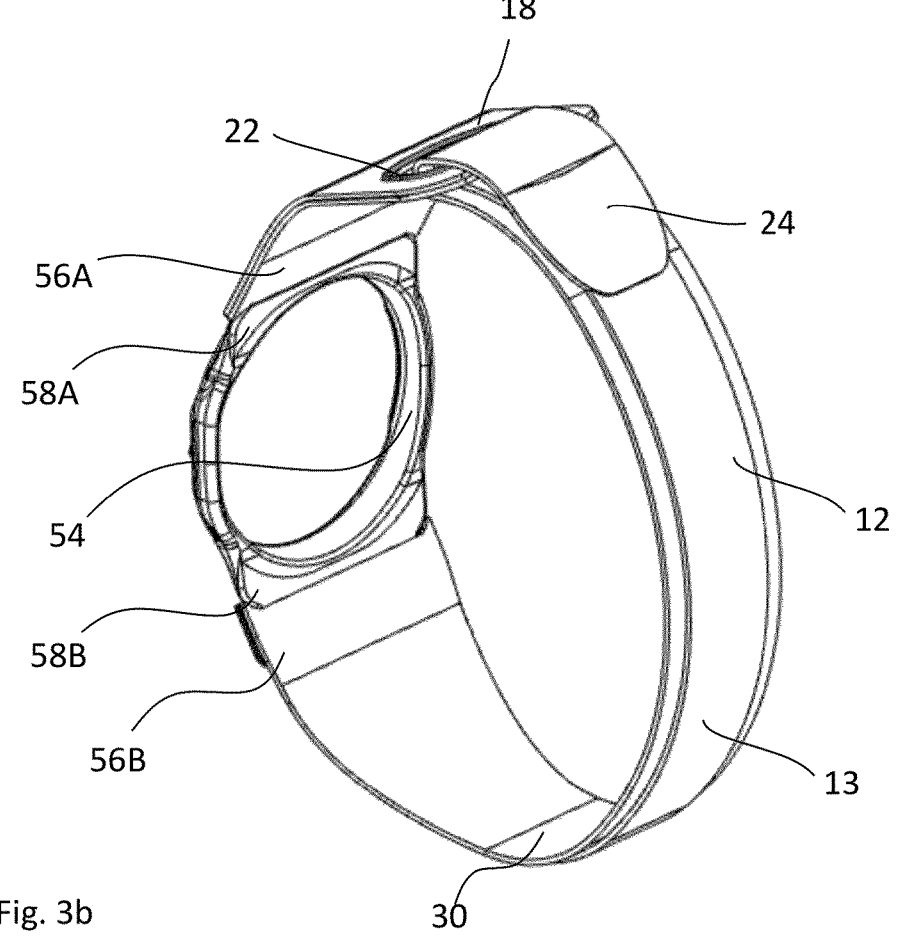
Figure 4:
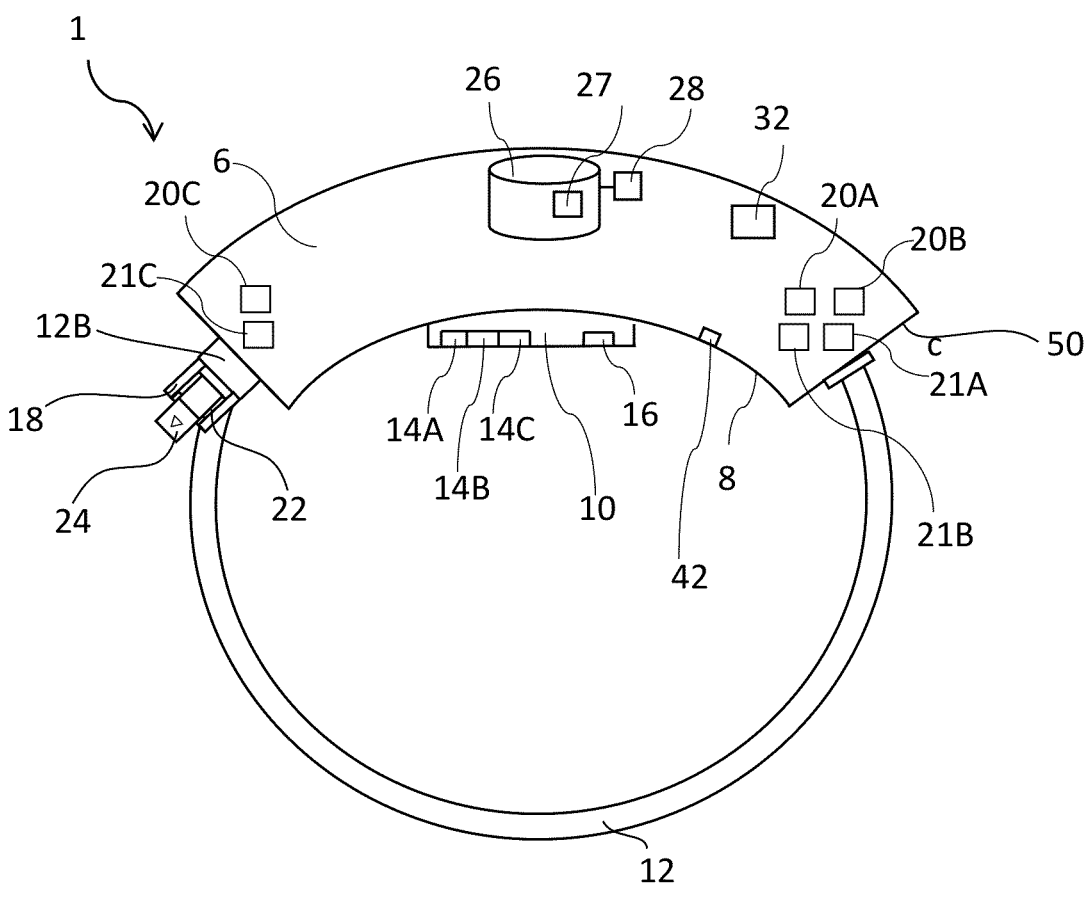
FIG. 4 is a cross-sectional diagram of an apparatus including a unit and a strap.
Figure 5A:
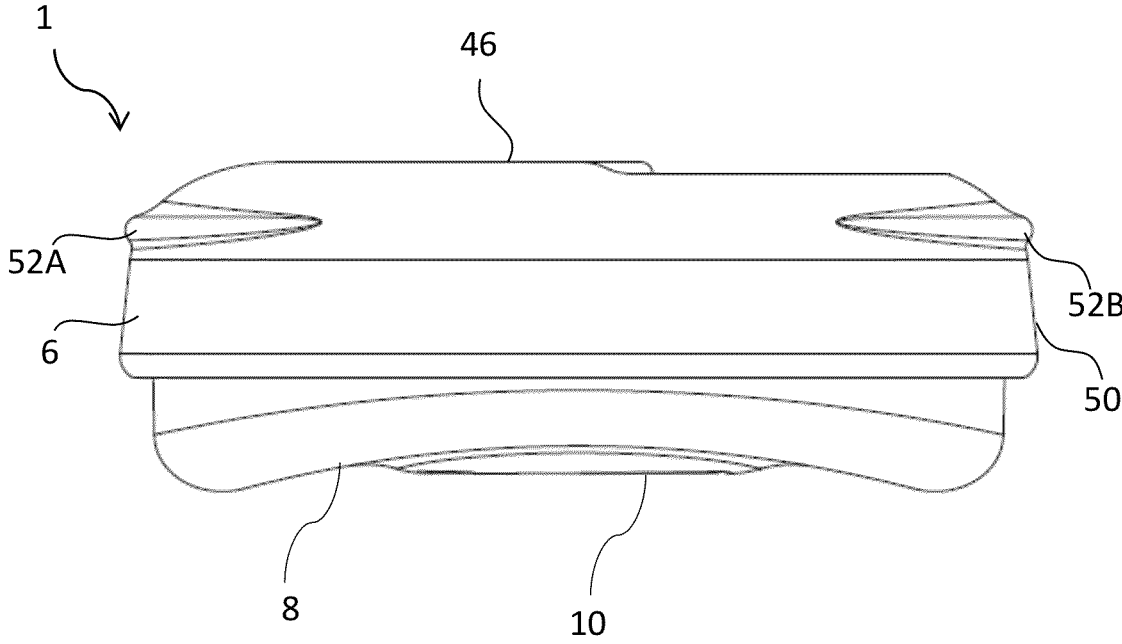
Figure 5B:
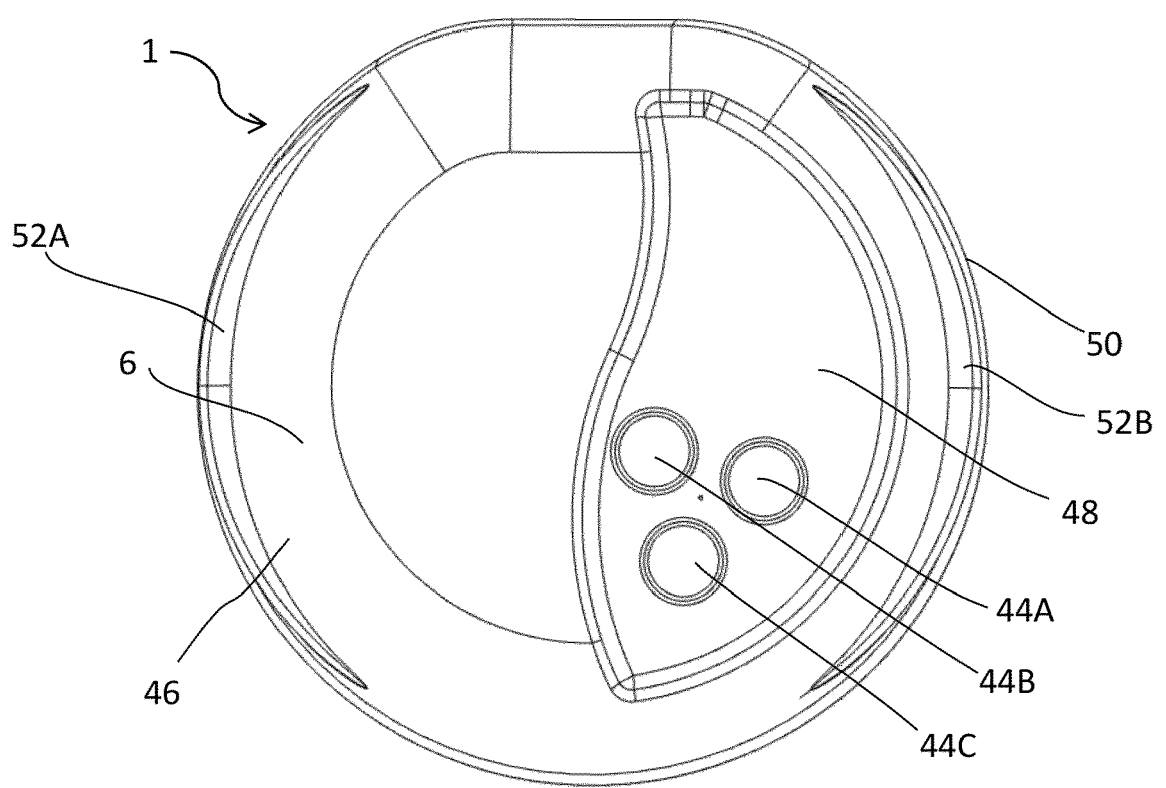
Figure 5C:
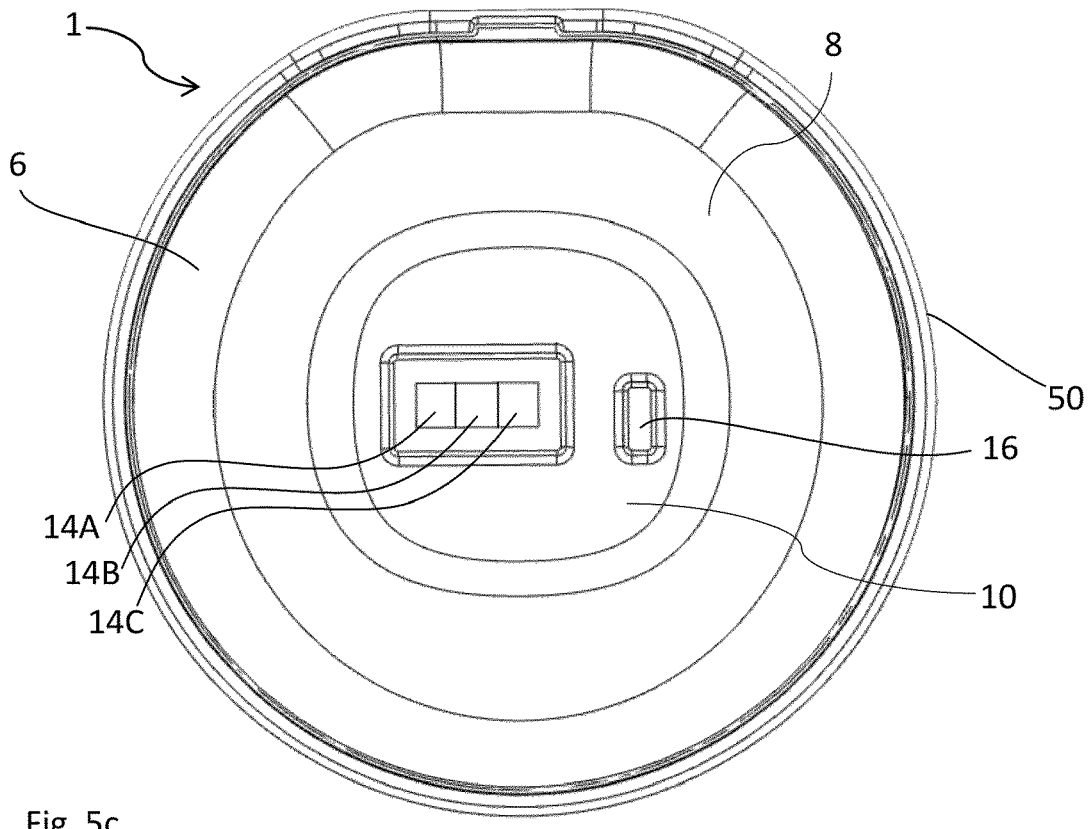

The rounded outer perimeter wall 50 has two connecting portions 52A, 52B arranged to cooperate with a unit receiving portion 54 of a strap 12 (see FIGS. 3a and 3b). As well as the unit receiving portion 54, the strap 12 has a flexible strap portion 13, first and second stabiliser portions 56A, 56B, and a fastener 18 to hold the unit 1 in place on the upper arm 2 of the subject 4 during use. In this example, the fastener is formed from a loop 22 in the first stabiliser portion 56A. The end 24 of the first strap portion 12A can be passed through this loop 22 and doubled back on itself. The end 24 of the first strap portion is magnetic and is magnetically attracted to ferrous elements within the flexible strap portion 13, and the end 24 can therefore be held in position in such a way that the strap 12 can be comfortably adjusted to fit around the upper arm 2 of the subject without either overtightening or being too loose. The strap 12 has an elasticated region 30 which allows the strap to expand and contract in length as the arm 2 of the subject 4 moves. The first stabiliser portion 56A extends laterally from the unit receiving portion and second stabiliser portions 56B extends the unit receiving portion and the flexible portion 13. The first and second stabiliser portions 56A, 56B are less flexible than the flexible strap portion 13 and thus provide stabilisation of the unit 1 on the upper arm 2, in use.

The unit receiving portion 54 of the strap 12 has an aperture for receiving and retaining the unit, as well as first and second strap connectors 58A, 58B for connecting the strap 12 to the unit receiving portion 54 (e.g. via the first and second stabiliser portions 56A, 56B). Thus the strap 12 may be replaced in the event that it becomes worn. However, it will be understood that in some examples the unit receiving portion 54 may be integrally formed with the strap 12.

Figure 2:
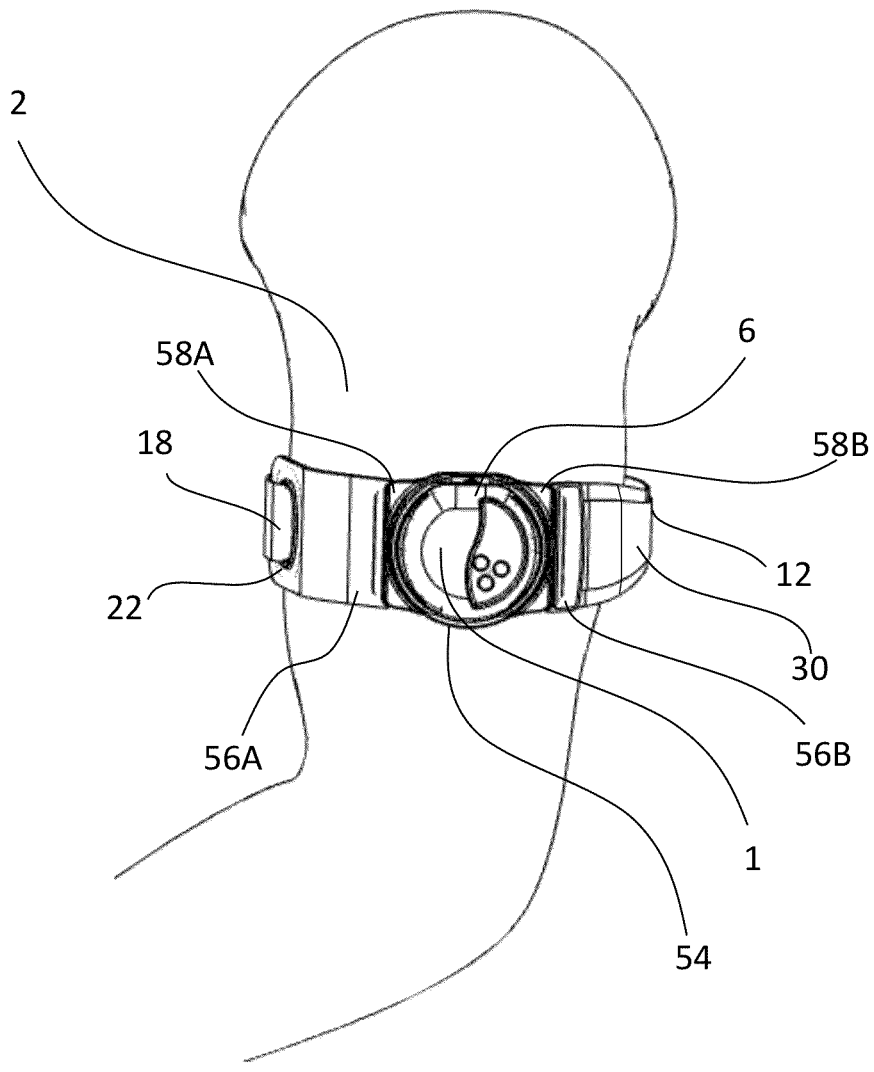
FIG. 2 is a diagram of the apparatus of FIG. 1 on the upper arm of a subject.

As can be seen from FIG. 2, the unit 1 is configured to be worn (e.g. held in place by the strap 12) on the outside of the upper arm 2 between the elbow and the shoulder.

A microprocessor 26, in electronic communication with a solid-state memory 28 controls the function of the unit, including controlling the LEDs and processing the measurements made by the gyroscopes 20A, 20B, 20C and accelerometers 21A, 21B, 21C (motion signals), and the measurements from the photosensor array 16 (photoplethysmograph (PPG) signals) and the temperature sensor 42. The microprocessor has a clock 27, which provides a common clock signal for sampling of both the motion signals and the photoplethysmograph signals. The memory 28 stores instructions which, when executed by the microprocessor 26, can cause the apparatus to determine an indicator of blood oxygen saturation in dependence on the photoplethysmograph data and to output the determined indicator of blood oxygen saturation.

Figure 17:
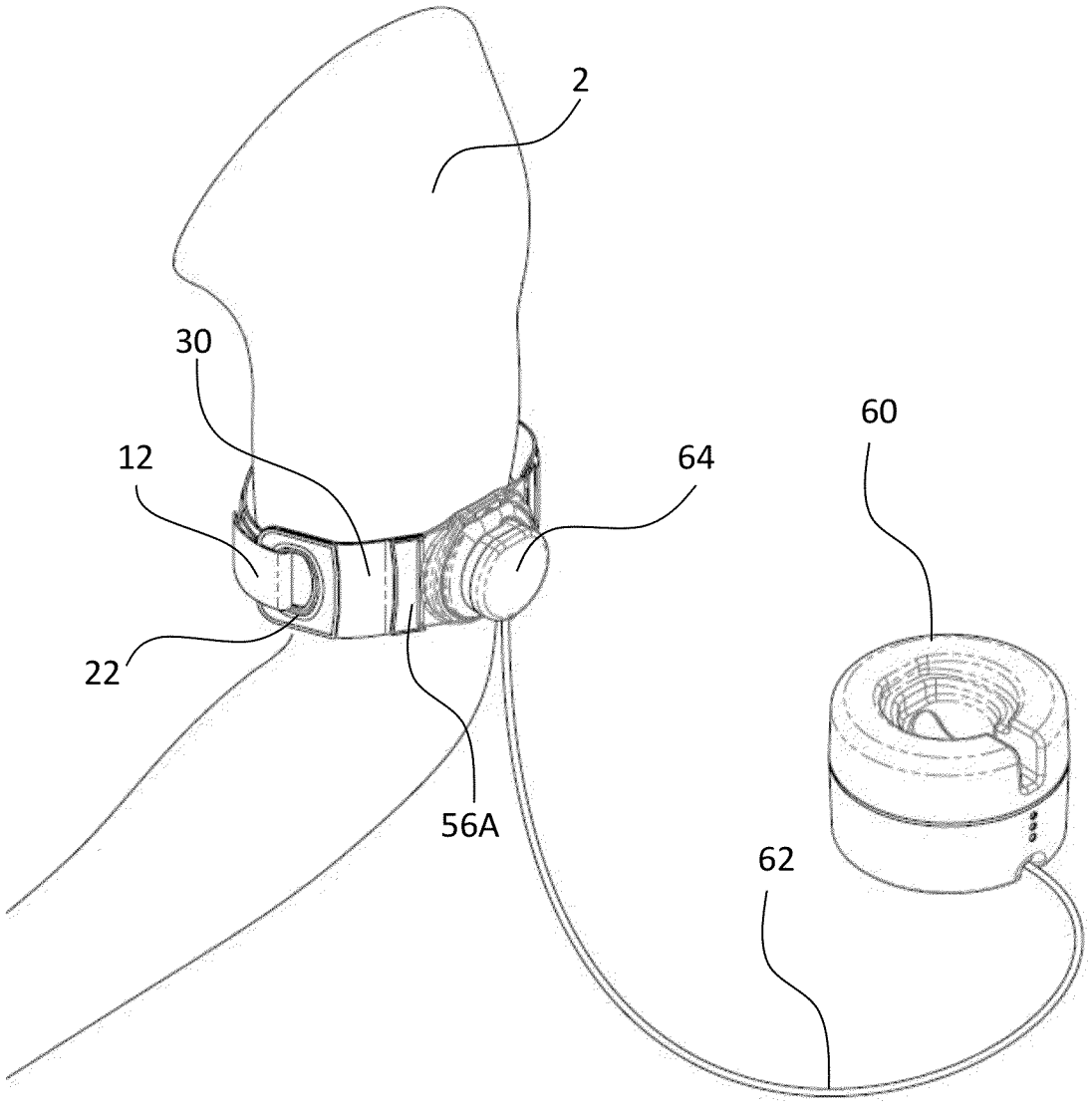
FIG. 17 is a diagram of the apparatus according to an aspect of the invention, on the upper arm of a subject, with a charger connected.

The unit 1 has an integral power supply 32, in the form of a rechargeable battery. As a result, the unit 1 is an ambulatory unit, in that the subject 4 is not restricted in motion by the need to have the unit 1 connected to a power supply via a power cable. The subject 4 can therefore walk about and carry out various day-to-day activities without needing to remove the unit 1. The planar outer surface 46 has a charger connector for connecting to a charger 60 to thereby charge the battery 32 (see FIG. 17). The unit 1 be removed from the arm 2 (and optionally the strap 12) and connected to the charger for charging. However, the charger 60 also has a connector 64 connected to the charger 60 via a power cable 62 as is shown in FIG. 17. Therefore, the unit 1 can be charged by connecting the connector 64 to the unit 1 while the unit 1 is still on the upper arm 2, therefore allowing charging to take place while the unit 1 is still worn, provided the subject 4 does not move far from the charger 60.

In use, light is emitted by the LEDs 14A, 14B, 14C and directed into the upper arm 2 of the subject 4. Blood vessels and other tissues within the upper arm 2 absorb a portion of the light from the LEDs 14A, 14B, 14C and a portion of the light is reflected by the blood vessels and other tissues, back towards the unit 1. The reflected light is detected by the photosensors in the photosensor array 16 and is thus captured as photoplethysmograph (PPG) data. The photoplethysmograph data is time series data including wavelength and intensity measurements of the reflected light received by the photosensor array 16.

Figure 7:
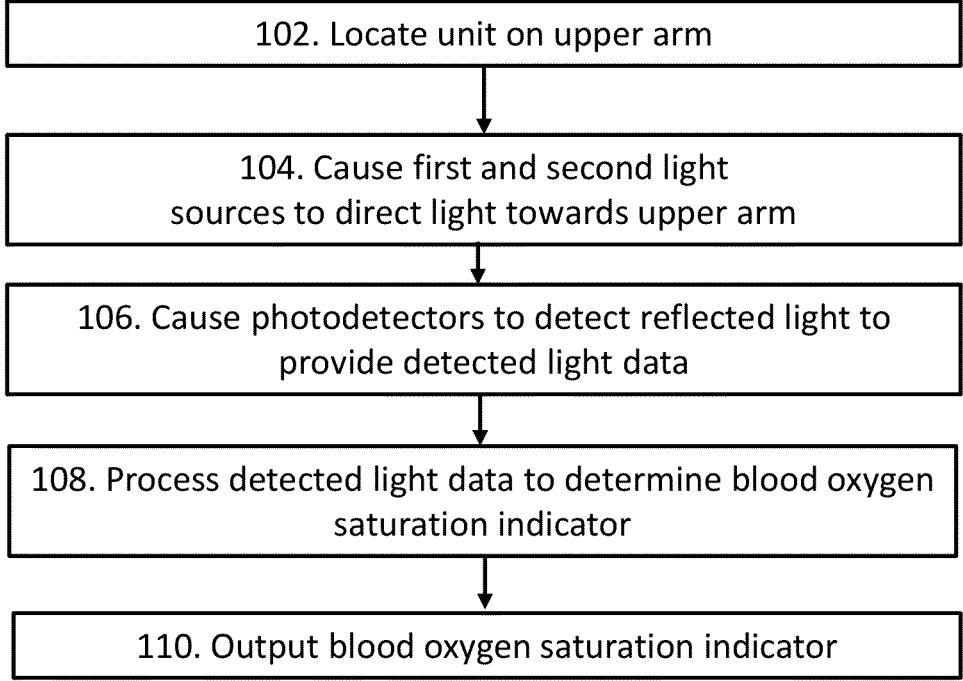
FIG. 7 is a flowchart of steps in an example of a method according to the invention.

FIG. 7 is a flowchart of example steps in a method of use of the apparatus according to the invention. Here, the steps include:

102: locating the unit on the upper arm;
  104: causing the first and second light sources to direct light towards the upper arm;
  106: causing the photodetectors in the photodetector array to detect light reflected from within the upper arm, to thereby provided detected light signals from detected light data;

108: processing the detected light data to determine an indicator of blood oxygen saturation; and

110: outputting the indicator of blood oxygen saturation.

Steps 104 to 110 are repeated periodically, provided that the light signals are reliable and accurate enough to provide a reliable and accurate determination of the indicator of blood oxygen saturation. Where the light signals are not sufficiently reliable or accurate, steps 108 and/or 110 may be omitted.

Figure 8:
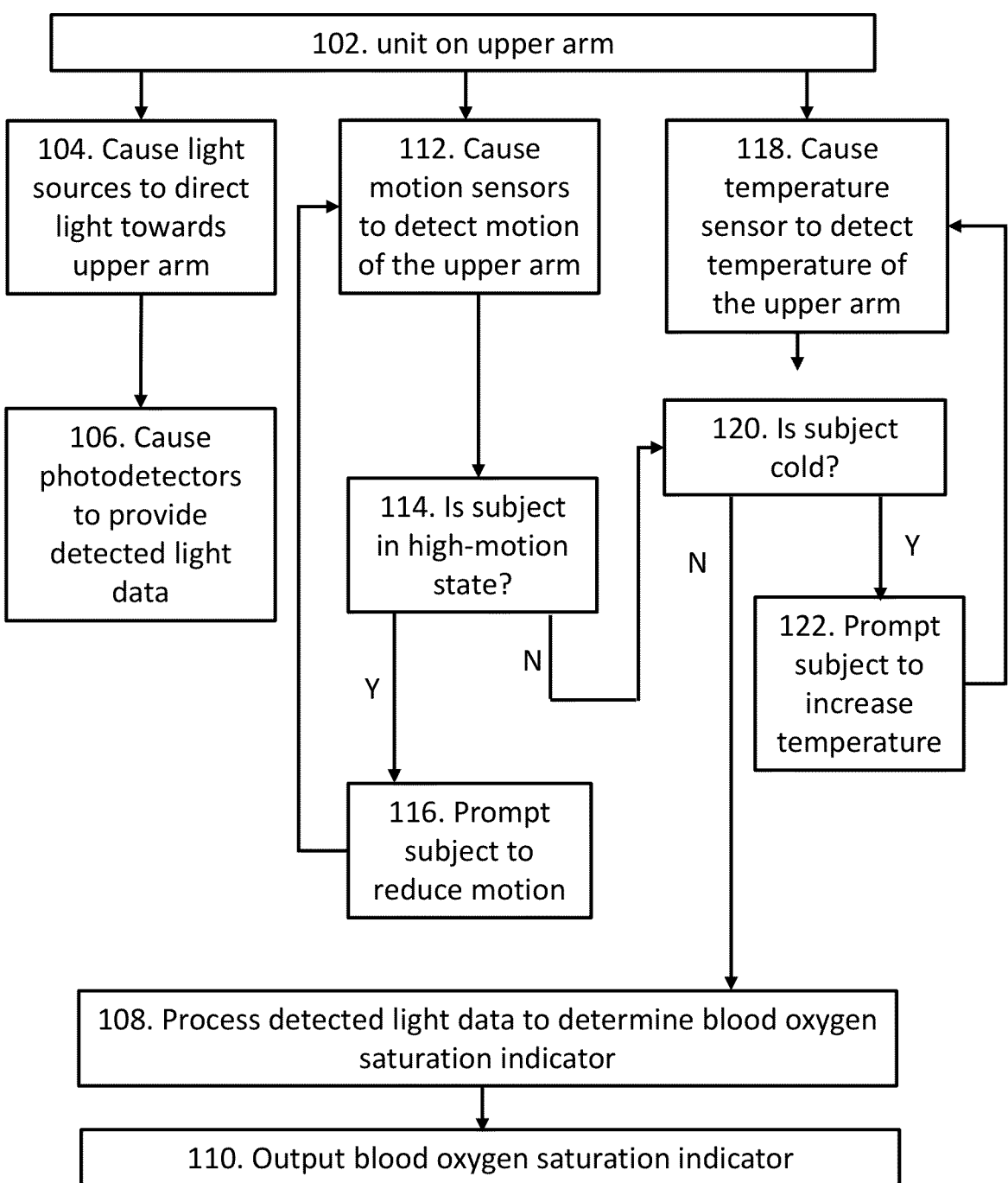
FIG. 8 is a flowchart of steps in an example of a method according to the invention.

FIG. 8 is a flowchart of example steps in a method of use of the apparatus according to the invention, including some additional steps beyond those shown in FIG. 7. Here, the method includes use of motion sensor data and temperature sensor data to determine whether the light signals are reliable and accurate enough to provide a reliable and accurate determination of the indicator of blood oxygen saturation. As such, as well as steps 102 to 110, this example method also includes the following steps:

112: Causing the motion sensors (e.g. the gyroscopes 20A, 20B, 20C and accelerometers 21A, 21B, 21C) to detect motion of the upper arm;

114: Using the resulting motion data to determine whether the subject is in a high-motion state; and if so

116: Prompting the subject to reduce their motion.

In addition, the method also includes the following steps:

118: Causing the temperature sensor to detect the temperature of the upper arm;

120: Using the resulting temperature data to determine whether the subject is cold; and if so

122: Prompting the subject to increase their temperature.

Although steps 112 to 116 and steps 118 and 122 may be optional, they can be helpful in improving the quality of the light signals and therefore the determined indicator of blood oxygen saturation. In some examples, steps 108 and 110 may not be carried out unless the subject is not determined to be in a high-motion state and is not determined to be cold.

Figure 11:
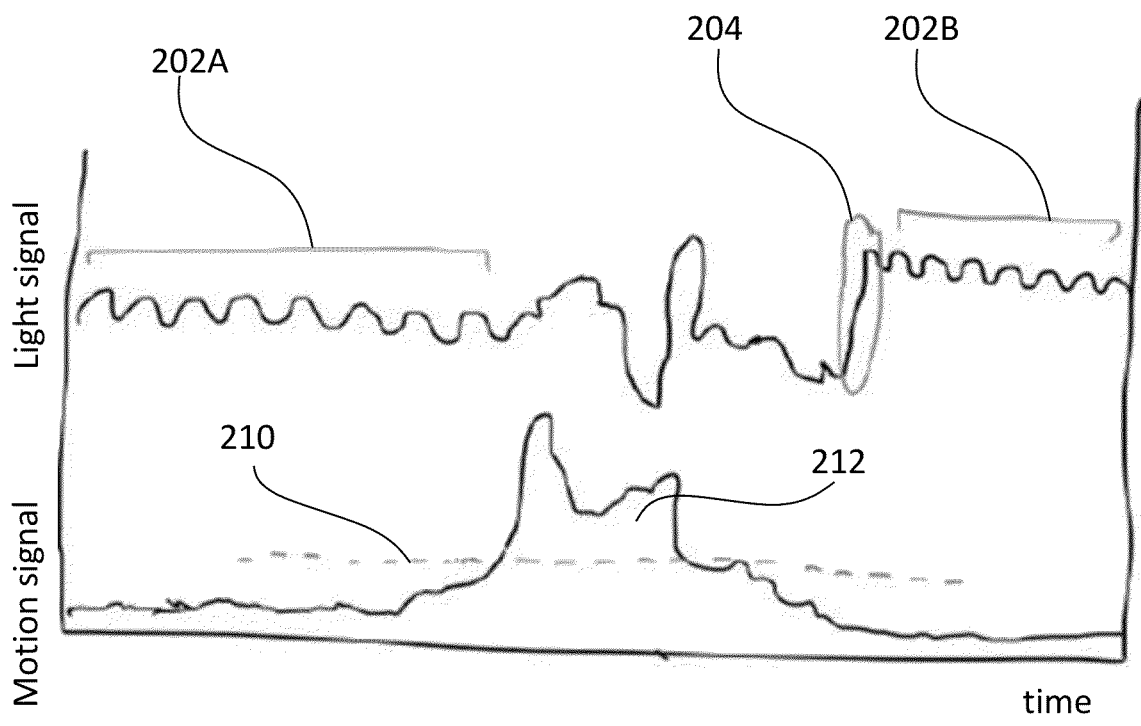
FIG. 11 is a sketch of a graph of light signal waveforms and motion signal as a function of time in a hypothetical example dataset.

In some example embodiments of the invention, where an indicator of blood oxygen saturation is determined, further processing may take place to determine an estimate of blood oxygen saturation and the method includes outputting the determined estimate of blood oxygen saturation. For example, referring to FIG. 11 which is a sketch of a graph of light signal waveforms and a motion signal as a function of time in a hypothetical example dataset, it can be seen that when the subject is in a high-motion state this negatively affects the light signal data. Here, a first low motion light signal 202A is acquired whilst the subject's motion is below a maximum tolerable motion level 210. This low motion light signal 202A being generally sinusoidal. Following this, the light signal data is noisy during a high-motion period 212 (above the maximum tolerable motion level 210) where the signal is irregular. When the subject's motion is reduced, sensor re-calibration 204 is carried out to acquire a high-quality signal and a second low motion light signal 202B is subsequently acquired, the low motion signal 202B again being generally sinusoidal.

Figure 6:
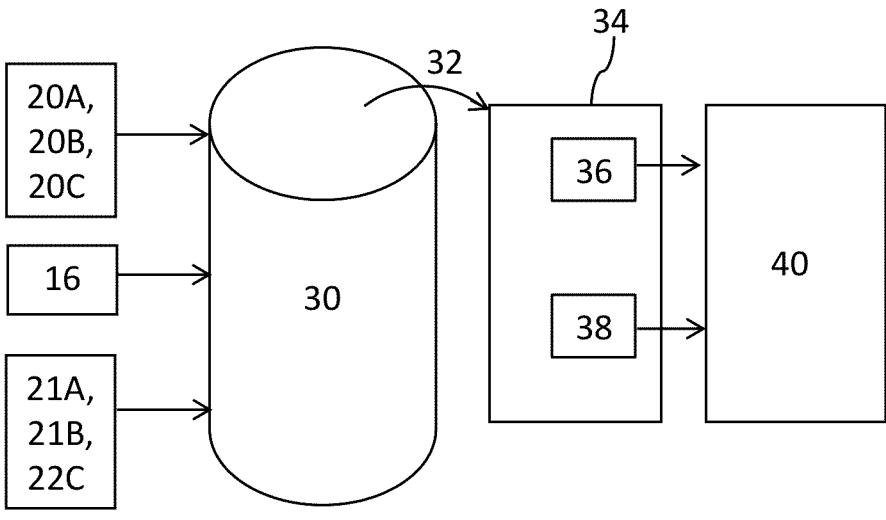
FIG. 6 is a flowchart of an example operating method according to the invention.

A general operating procedure of the monitor is shown in overview in FIG. 6. Measurements are recorded from the photosensor array 16, the first, second, and third gyroscopes 20A, 20B, 20C and the first, second, and third accelerometers 21A, 21B, 21C. The measurements are made periodically and frequently, in this example at 50 Hz, and the resulting gyroscope motion data, accelerometer motion data and photoplethysmograph measurement data are stored as a time series in a database 30 in the solid-state memory 28 for subsequent processing.

Periodically, the stored gyroscope data, stored accelerometer data and the stored photoplethysmograph data for a window of time are extracted 32 from the database by the microprocessor 26 and are processed to determine an estimate of blood oxygen saturation. The resulting data 34 for a specific time window comprises a time series of motion signal data 36 (a combination of the rotation around each of the three axes and the acceleration along three axes) and a photoplethysmograph signal 38. One skilled in the art will appreciate that the units in which these values are expressed is a matter of design choice.

In an example, each window relates to 8 seconds of data samples at a sampling frequency of 50 Hz, i.e. 400 samples per motion sensor, per temperature sensor and per photodetector. The concurrency of corresponding data windows (e.g. a window of motion signal data and a corresponding window of photoplethysmograph signal data) is ensured by the use of a common clock signal.

The said windows of data are then processed 40. The processing includes analysis of the motion signal data and the photoplethysmograph data to determine whether suitable data for determining an estimate of blood oxygen saturation has been obtained. If suitable data for determining an estimate of blood oxygen saturation has been obtained, such an estimate is then determined and is output.

In some cases, for example when the subject 4 is in a high movement state, a given window of data will contain noise. As this could lead to an unreliable estimate of blood oxygen saturation, windows of data containing more than a predetermined threshold level of noise are rejected and not used in blood oxygen saturation estimate calculations. However, such windows of data are still stored for optional subsequent processing, e.g. via a machine learning algorithm.

Figure 9:
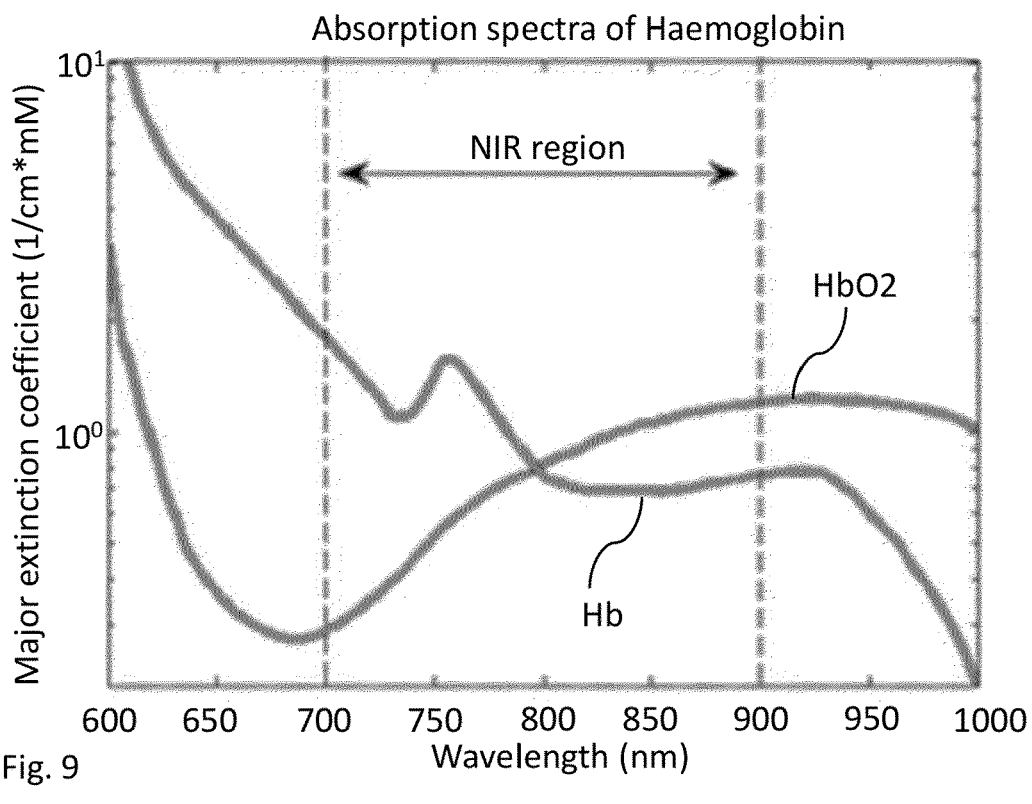
FIG. 9 is a graph of absorption spectra of haemoglobin.

FIG. 9 is a graph of the absorption spectra of haemoglobin and oxyhaemoglobin. As can be seen from this graph, the absorption of light by haemoglobin by oxyhaemoglobin varies non-linearly as a function of wavelength. Furthermore, except near 800 nanometres, haemoglobin and oxyhaemoglobin absorb different proportions of incident light. As a result, the difference in the intensities of reflected red and infrared light can be used to estimate an indicator of blood oxygen saturation. To do this, the waveforms of data from the photosensor array 16 (photoplethysmograph data) must be processed.

Figure 10:
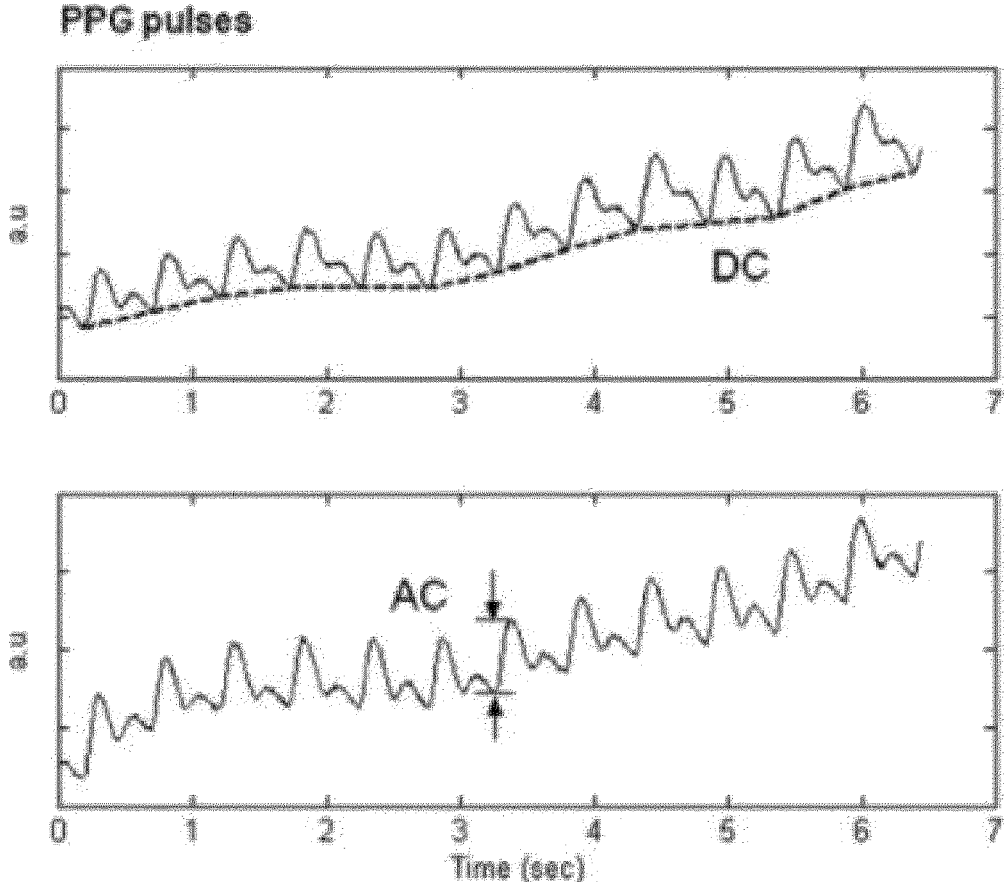
FIG. 10 is a pair of graphs of the AC and DC components of photoplethysmograph data.

FIG. 10 is a pair of graphs showing examples of red (upper plot) and infrared (lower plot) photoplethysmograph data in a time series. The AC (frequency-dependent) and DC (frequency-independent) components of these waveforms are highlighted. The AC variation is caused by the arterial pulse, which modulates the amount of arterial blood (i.e. oxygenated blood and thus oxyhaemoglobin) in the field of view of the photodiode array 16.

In an example, the AC and DC components in synchronous samples of red and infrared photoplethysmograph data are determined and the ratio of ratios, R, is calculated according to the following equation:

$$R = \frac{AC_{red}/DC_{red}}{AC_{infrared}/DC_{infrared}}$$

As blood oxygen saturation changes, so does R. As such, either R can be output as an indicator of blood oxygen saturation, or R can be further processed to determine a blood oxygen saturation estimate in the form of an $SpO_2$ (oxygen saturation in peripheral arterial blood) percentage.

In which case, this value of R is compared to a device-specific calibration model derived from controlled studies. The inclusion of the DC components in the above calculation compensates for differences in the optical efficiency of the red and infrared input wavelengths. For example, depending on the subject's skin tone, more or less red light may be absorbed by the skin and thus correspondingly less red light may penetrate into the upper arm. However, this effect will be relatively constant and so can be compensated for by the DC components in the ratio.

Figure 12A:
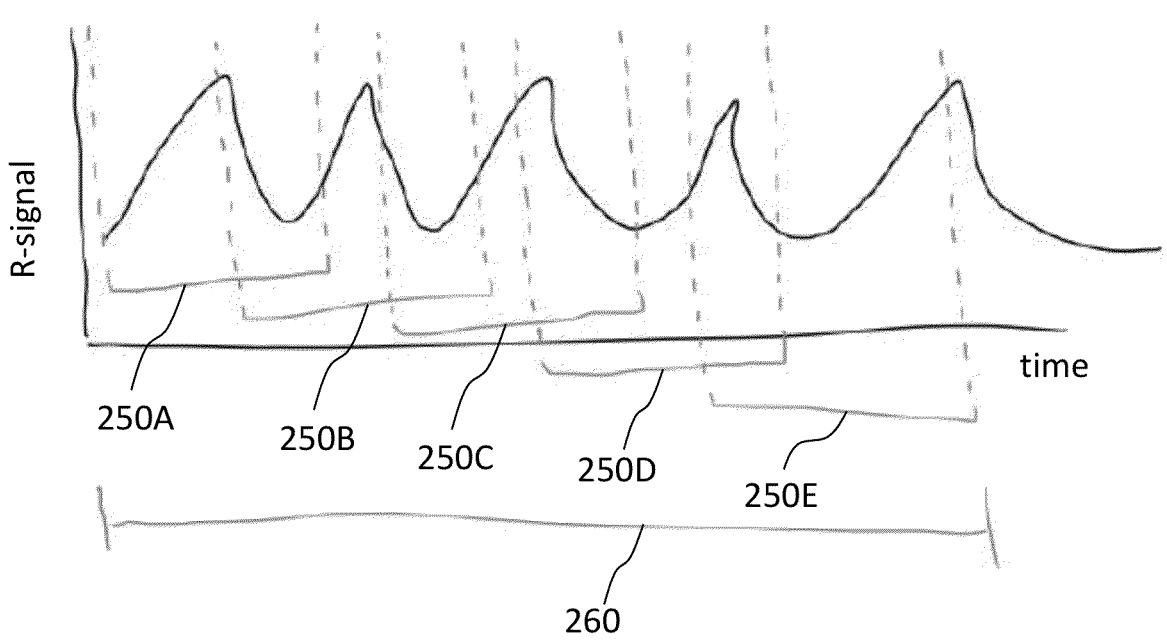
FIGS. 12a and 12b are sketches of graphs of pulse waveforms as a function of time over hypothetical example measurement periods.
Figure 13A:
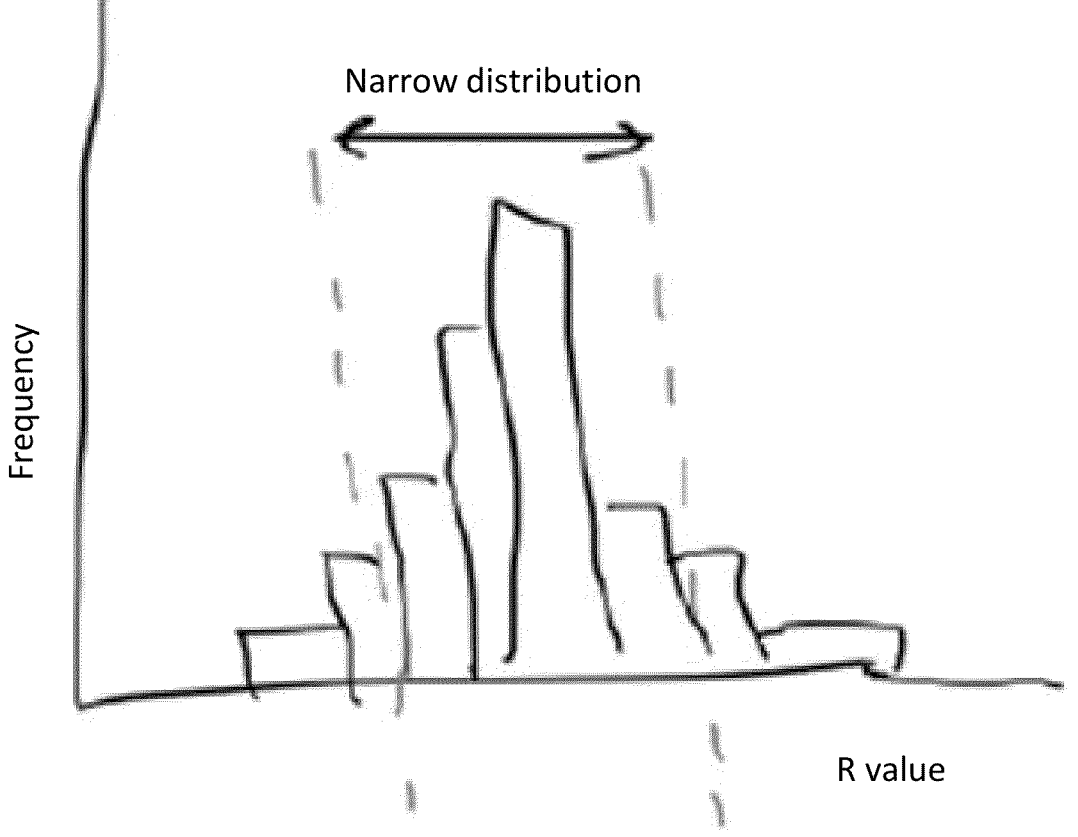
FIGS. 13a and 13b are sketches of histograms of hypothetical example datasets corresponding to the respective hypothetical example measurement periods of FIGS. 12a and 12b.

Referring to FIG. 12A, which is a sketch of a graph of a pulse waveform as a function of time over a hypothetical example measurement, in order to determine whether the R-signal is "high quality" or "low quality", an 8-second sample of data 260 is divided into multiple windows 250A, 250B, 250C, 250D, 250E. R is then calculated for each of the windows 250A, 250B, 250C, 250D, 250E and, in this example, the calculated R values are plotted in a histogram. Refer to FIG. 13A which is a sketch of a histogram of R values corresponding the data in the windows 250A, 250B, 250C, 250D, 250E of FIG. 12A. The histogram of FIG. 13A has a narrow distribution, and the distribution is symmetric around the median value of R, as would be expected where the motion signals are reliable. The narrow distribution of R values in the histogram of FIG. 13A is indicative of a stable and distinct signal within expected boundaries for human physiology. Such a histogram can then be used to find the median R value and this can be used to determine an indicator of blood oxygen saturation based on device-specific calibration. The skilled person will appreciate that there are other ways of determining the distribution of data which would also be appropriate, and that the invention is not therefore restricted to the use of histograms.

Figure 12B:
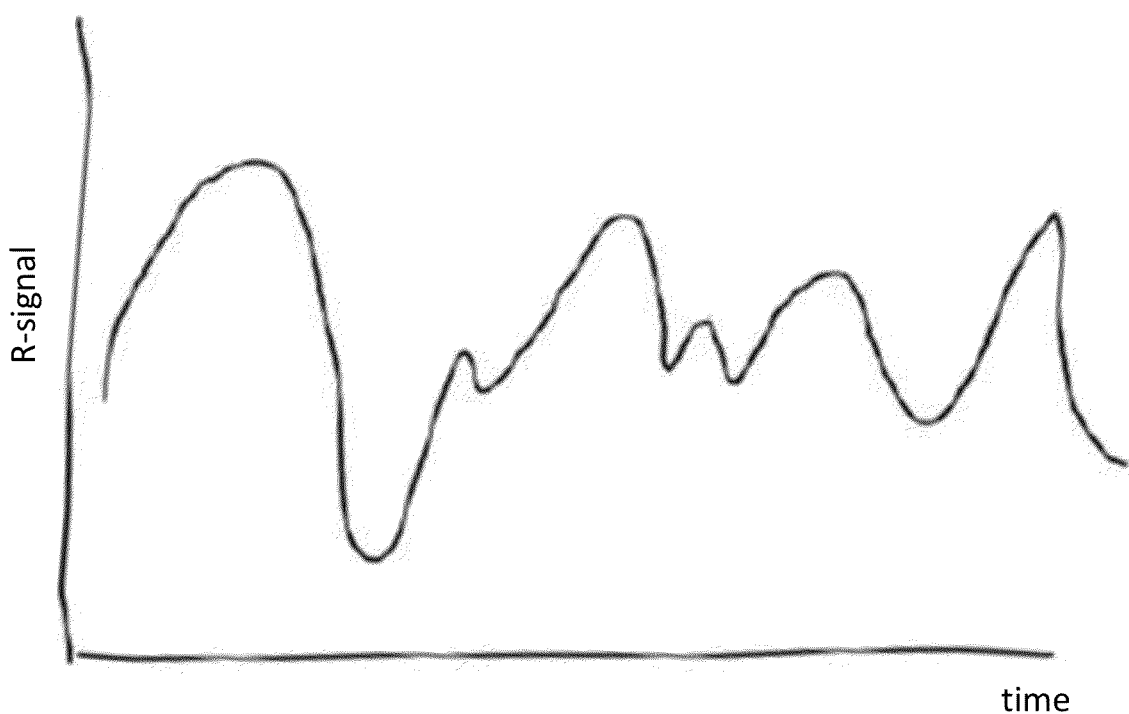
Figure 13B:
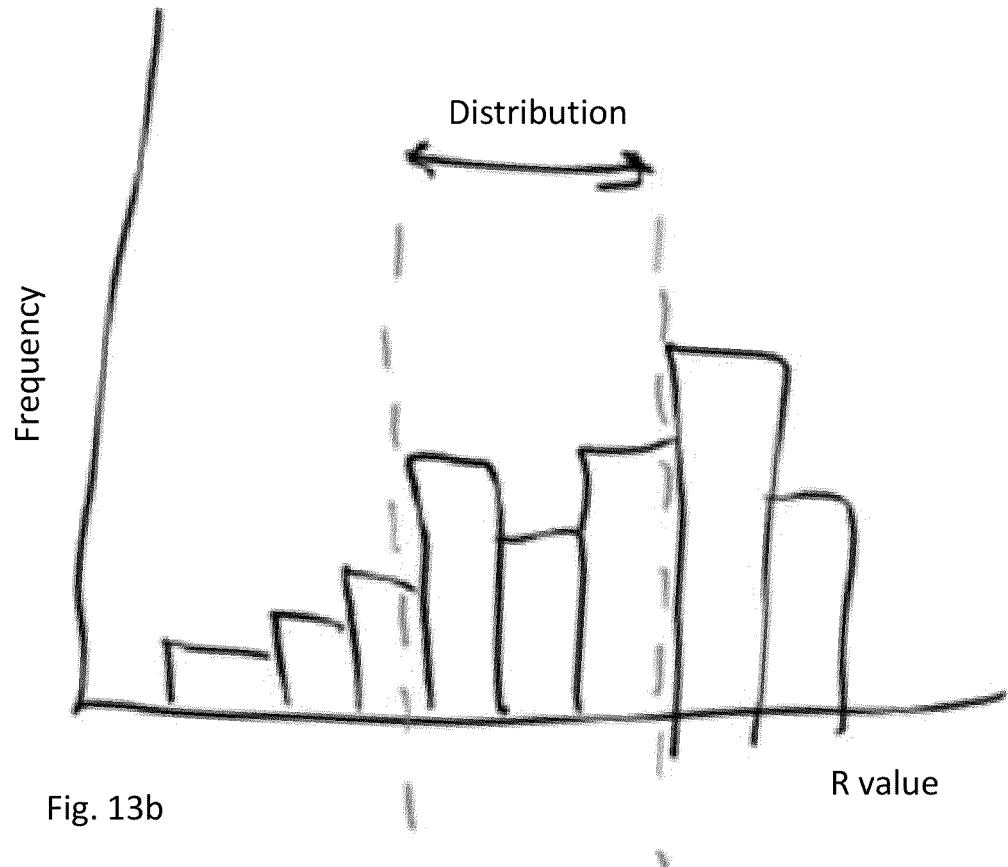

Referring to FIG. 12B, which is another sketch of a graph of a pulse waveform as a function of time over a hypothetical example measurement, in this case where the R-signal is noisy. The corresponding histogram for FIG. 12B (see FIG. 13B for a sketch of such a histogram) will have a wide distribution and may not be symmetrical around the median R value. As this can clearly be seen from the resulting histogram, a decision can be made on this basis to not calculate, or not output, an indicator of blood oxygen saturation.

Figure 14:
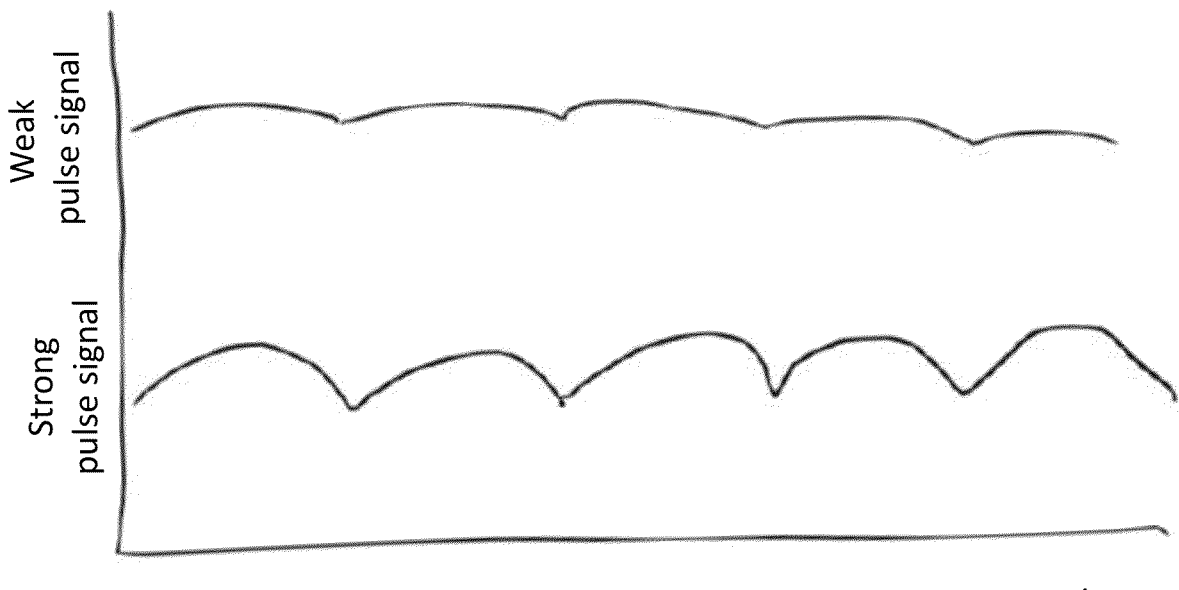
FIG. 14 is a sketch of a graph of a hypothetical example weak pulse signal and a hypothetical example strong pulse signal.

FIG. 14 is a sketch of a graph of a hypothetical example weak pulse signal and a hypothetical example strong pulse signal. A weak pulse signal can be recovered using digital processing along with the above-described method of dividing the data into windows and considering a histogram of the data of the said windows.

Figure 15:
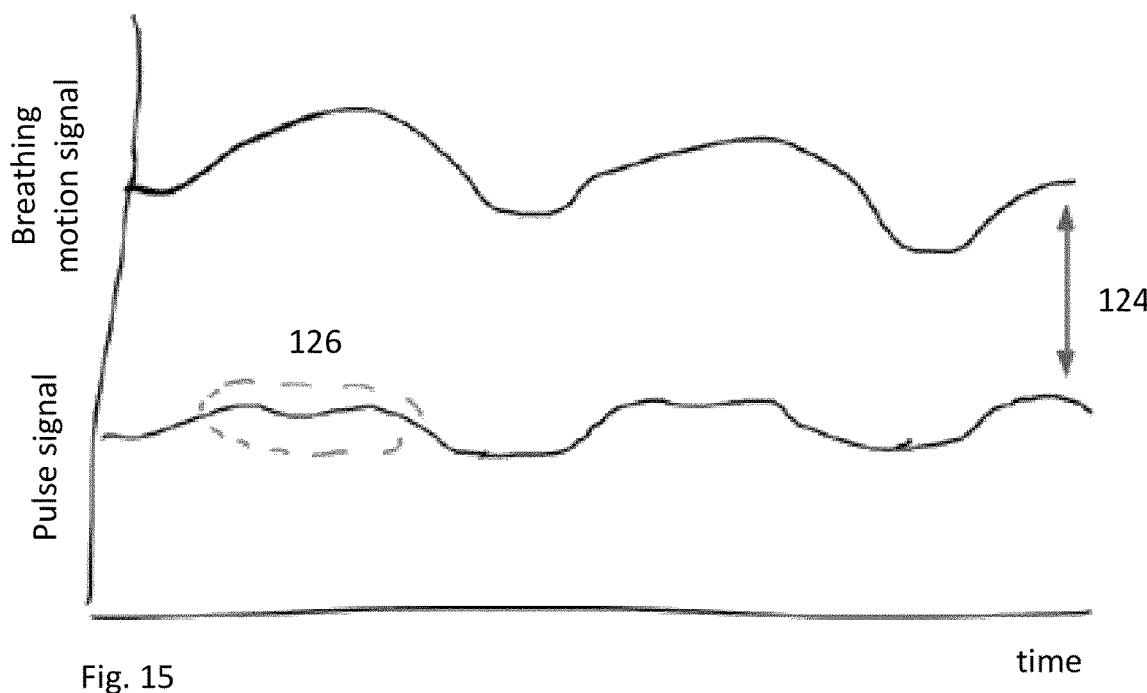
FIG. 15 is a sketch of a graph of a hypothetical example breathing motion signal and a corresponding hypothetical example pulse signal dominated by breathing motion.

On the other hand, where the pulse signal is weak and the unit 1 is poorly coupled to the arm 2, for example, the mechanical motion of breathing by the subject can modulate the weak pulse signal. This is because is the unit 1 is poorly coupled to the arm 2 this can allow the unit 1 to palpate against the skin during breathing motions. FIG. 15 is a sketch of a graph of a hypothetical example where a breathing motion signal is great enough to dominate a weak pulse signal, such that the breathing motion signal might be mistaken for the pulse signal. There is a high correlation 122 in such cases between the motion signal and the pulse signal. The small pulse signal 124 hidden in the breathing signal cannot then be recovered by signal processing.

This problem is addressed by comparing the correlation between the motion signals from the motion sensors and the photoplethysmograph signals. As these two signals are independent of each other they should ordinarily not be correlated. Therefore, where the two signals are strongly correlated (for example as measured by Pearson correlation coefficient) it can be determined that motion (e.g. breathing motion) is great enough to interfere with the pulse signal a decision can be made on this basis to not calculate, or not output, an indicator of blood oxygen saturation. In this case an alert may also be created to prompt the subject 4 to take action to reduce the movement of the unit 1 relative to the arm 2, for example by re-positioning the unit 1 or tightening the strap 12.

Figure 16:
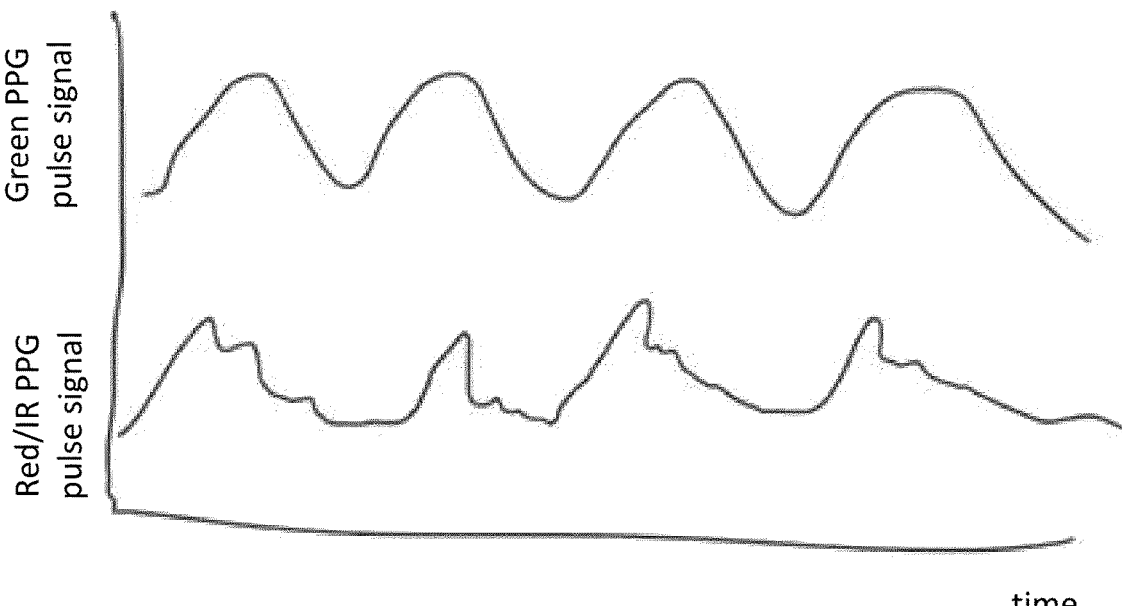
FIG. 16 is a sketch of a graph of a hypothetical example green photoplethysmograph pulse signal and a hypothetical example red or infrared photoplethysmograph pulse signal.

FIG. 16 is a sketch of a graph of a hypothetical example green photoplethysmograph pulse signal and a hypothetical example red or infrared photoplethysmograph pulse signal. In this example, the unit 1 has been placed over a vein. Green light rarely penetrates deep enough into to arm to reach the veins and therefore the green PPG pulse signal is a relatively clean, generally sinusoidal "arterial" waveform. In contrast, the red or infrared light penetrates deeper into the tissues over the arm and so can be absorbed and reflected by the vein that, in this case, the unit 1 has been positioned over. The result of this is that the red or infrared PPG signal is a more complex signal than the green one, as a result of the motion caused by venous pulsation. Using a venous PPG measurement rather than an arterial PPG measurement will lead to a falsely low determined indicator of blood oxygen saturation.

To address this, the green and red or infrared PPG signals are compared (e.g. correlated). If the unit 1 is not over a vein, the two signals should have similar morphology. If the comparison indicates that this is not the case (e.g. if the signals are only minimally correlated) a decision can be made on this basis to not calculate, or not output, an indicator of blood oxygen saturation. In this case an alert may also be created to prompt the subject 4 to take action to re-positioning the unit 1.

Throughout the description and claims of this specification, the words "comprise" and "contain" and variations of them mean "including but not limited to", and they are not intended to and do not exclude other components, integers, or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, or groups described in conjunction with a particular aspect, embodiment, or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The invention claimed is:

1. A method of monitoring blood oxygen saturation of a subject using an apparatus for monitoring blood oxygen saturation of a subject, the apparatus comprising:

a unit configured for wearing on the subject's upper arm, the unit comprising:

a first light source configured to direct light of a first wavelength towards the upper arm when the unit is worn on the upper arm;

a second light source configured to direct light of a second wavelength towards the upper arm when the unit is worn on the upper arm, the second wavelength being different to the first wavelength; and one or more photodetectors, each configured to output at least one detected light signal indicative separately of detection of light of the first wavelength and light of the second wavelength reflected from within the upper arm when the unit is worn on the upper arm;

one or more processors; and a memory including instructions which, when executed by the one or more processors, causes the apparatus to:

determine an indicator of blood oxygen saturation of blood in the upper arm, in dependence on the at least one detected light signal; and output the indicator of blood oxygen saturation, and the method comprising:

causing the first and second light sources to direct light towards the upper arm;

causing at least one of the one or more photodetectors to detect reflected light and to thereby output at least one detected light signal indicative separately of detection of light of the first wavelength and light of the second wavelength reflected from within the upper arm, wherein detection of light of the first wavelength is determined independently from detection of light of the second wavelength;

processing the at least one detected light signal to thereby determine an indicator of blood oxygen saturation of blood in the upper arm; and wherein the method further comprises determining how much the indicator of blood oxygen saturation varies across a measurement period and outputting the determined indicator of blood oxygen saturation only when the indicator is indicative of a change of less than ±5 percent within a measurement period of at least 8 seconds.

2. A method according to claim 1, wherein the method comprises processing the determined indicator of blood oxygen saturation of blood in the upper arm to determine an estimate of blood oxygen saturation of the subject and outputting the determined estimate of blood oxygen saturation of the subject.

3. A method according to claim 1, wherein the unit comprises a motion sensor configured to output a detected motion signal indicative of motion of the unit, and wherein the memory includes instructions which, when executed by the one or more processors, causes the apparatus to determine an indicator of blood oxygen saturation of blood in the upper arm in dependence on the at least one detected light signal and the detected motion signal and/or to output the indicator of blood oxygen saturation in dependence on the detected motion signal, and wherein the method comprises:

processing the detected motion signal and the at least one detected light signal to determine whether the subject is moving enough to cause the determined indicator of blood oxygen saturation to be unreliable; and outputting the determined indicator of blood oxygen saturation in dependence on whether the determined indicator of blood oxygen saturation of the subject is determined to be unreliable.

4. A method according to claim 1, wherein the at least one detected light signal comprises a first and second wavelength signal components, indicative of light of the first and second wavelengths received by the one or more photodetectors, and wherein processing the at least one detected light signal comprises:

determining a frequency-dependent component of the first wavelength signal component;

determining a frequency-independent component of the first wavelength signal component;

determining a first ratio, where the first ratio is a ratio of the frequency-dependent component to the frequency-independent component of the first wavelength signal component;

determining a frequency-dependent component of the second wavelength signal component;

determining a frequency-independent component of the second wavelength signal component;

determining a second ratio, wherein the second ratio is a ratio of the frequency-dependent component to the frequency-independent component of the second wavelength signal component; and determining the ratio of the first ratio to the second ratio.

5. A method according to claim 1, wherein the unit comprises a temperature sensor configured to output a temperature signal indicative of the temperature of the subject's upper arm when the unit is worn on the subject's upper arm, and wherein the method further comprises generating an alert to cause the subject to take an action to raise their temperature, if the temperature signal is indicative of a temperature below a predetermined threshold temperature.

6. A method according to claim 5, wherein the determined indicator of blood oxygen saturation is not deleted or discarded when determined to be unreliable and wherein the method comprises recording the determined indicator of blood oxygen saturation for further analysis.

7. A method according to claim 1, wherein the method comprises outputting the determined indicator of blood oxygen saturation only if the determined indicator of blood oxygen saturation is determined to be not unreliable.

8. A method according to claim 1, wherein the measurement period is less than 25 seconds.

* * * * *